United States Patent [19]

Gauthier et al.

[11] Patent Number: 4,976,683

[45] Date of Patent: Dec. 11, 1990

[54] PERITONEAL DIALYSIS METHOD

[75] Inventors: Robert J. Gauthier, Lake Forest, Ill.; Robert S. Levinson, Saline, Mich.

[73] Assignee: Abbott Laboratories, Abbott Park, Ill.

[21] Appl. No.: 220,779

[22] Filed: Jul. 18, 1988

Related U.S. Application Data

[63] Continuation-in-part of Ser. No. 876,941, Jun. 20, 1986, abandoned.

[51] Int. Cl.$^5$ .............................................. A61M 1/00
[52] U.S. Cl. ....................................... 604/29; 604/27; 604/28
[58] Field of Search .................................. 604/27–29, 604/323, 411, 81, 892–894, 5

[56] References Cited

U.S. PATENT DOCUMENTS

| | | | |
|---|---|---|---|
| 3,545,438 | 12/1970 | DeVries | 604/28 |
| 3,911,915 | 10/1975 | Seifter et al. | 604/29 |
| 4,239,041 | 12/1980 | Popovich et al. | 604/29 |
| 4,306,976 | 12/1987 | Bazzato | 604/28 |
| 4,339,433 | 7/1982 | Kartinos et al. | 604/29 |
| 4,585,436 | 4/1986 | Davis et al. | 604/29 |

FOREIGN PATENT DOCUMENTS

| | | | |
|---|---|---|---|
| 0089135 | 9/1983 | European Pat. Off. | 604/29 |
| 8505555 | 12/1985 | PCT Int'l Appl. | 604/28 |
| 2132914 | 7/1984 | United Kingdom | 604/29 |

*Primary Examiner*—Stephen C. Pellegrino
*Assistant Examiner*—Michael Rafa
*Attorney, Agent, or Firm*—A. Nicholas Trausch

[57] ABSTRACT

This invention relates to an improved method for conducting peritoneal dialysis with a decreased total volume of dialysis fluid used and increased efficacy parameters such as ultrafiltration rate, urea clearance rate and dialysate volume as compared to conventional techniques. In the method of this invention, a fluid communication through the peritoneal membrane into the peritoneal cavity of a patient in need of peritoneal dialysis treatment is established. An initial volume of an aqueous peritoneal dialysis composition containing an osmotic agent is instilled into the peritoneal cavity through the fluid communication. The dialysis composition contains an amount of dissolved osmotic agent (i) that is insufficient to adequately dialyze the patient during a predetermined time period of dialysis treatment, but (ii) that is present at an osmolarity that is greater than the osmolarity of the body fluids in contact with the membrane, such that an osmolarity gradient is created across the membrane between the composition and the body fluids. A flux of water and solute enters the composition from the body fluids by means of that gradient.

A further amount of dissolved osmotic agent is released into the instilled dialysis composition to form a modified dialysis composition. That further osmotic agent is released in an amount sufficient to maintain a substantially constant osmolarity gradient between the modified dialysis composition and the body fluids such that the water and solute flux continues to enter into the modified dialysis composition during the predetermined dialysis time period. The modified dialysis composition is substantially removed from the peritoneal cavity at the end of the treatment time period.

24 Claims, 18 Drawing Sheets

COMPARISON OF EFFICACY PARAMETERS: REGULAR CAPD vs CONTROLLED RELEASE CAPD

| CONFIGURATION | TOTAL GRAM OF DEXTROSE ADMINISTERED OVER 6 HOURS (RABBIT) | AVERAGE ULTRAFILTRATION RATE OVER 6 HOURS (RABBIT) | ULTRAFILTRATION RATE AT 6 HOURS (RABBIT) | AVERAGE UREA CLEARANCE OVER 6 HOURS (RABBIT) | UREA CLEARANCE AT 6 HOURS DWELL (RABBIT) |
|---|---|---|---|---|---|
| INPERSOL 2.5% REGULAR CAPD 140ml VOLUME | 3.5 gram | 0.361 ml/min | -0.37 ml/min | 0.54 mg/min | 0.10 mg/min |
| INPERSOL 2.5% 140ml-FOLLOWED BY PUMP: D70W 2ml/hr | 11.9 gram | 0.56 ml/min (55.5% INCREASE) | 0.87 ml/min | 0.63 mg/min (18.8% INCREASE) | 0.18 mg/min (80% INCREASE) |
| INPERSOL 4.25% REGULAR CAPD 140ml VOLUME | 5.95 gram | N/A | N/A | N/A | N/A |

N/A= RABBIT DATA NOT AVAILABLE 8.5 gram FROM INITIAL INSTILLATION, PLUS 8.4 gram BY CONTROLLED RELEASE (AVE. OF 10 CONTROL AND 9 TEST ANIMALS)

FIG. 12

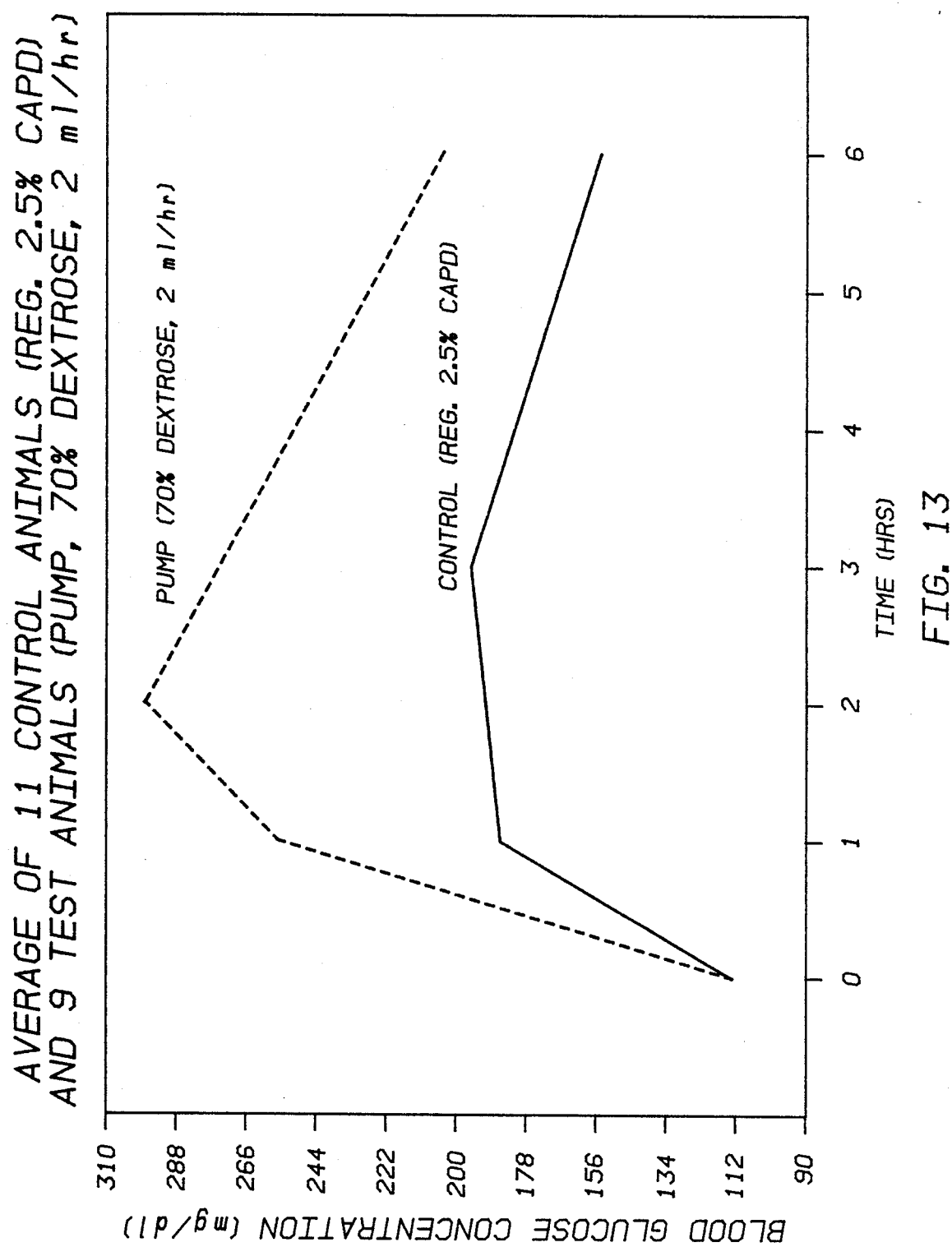

SUMMARY OF MAJOR FINDINGS
CONTROLLED RELEASE PERITONEAL DIALYSIS
PROOF OF PRINCIPLE

| STUDY PART | MAJOR FINDINGS |
|---|---|
| 1. EX. 3 ANIMAL STUDIES (PUMP) | ○ INCREASES IN ULTRAFILTRATION RATE, UREA CLEARANCE, AND DIALYSATE VOLUME SEEN OVER REGULAR CAPD. |
| 2. EX. 4 ANIMAL STUDIES (PUMP) | ○ INCREASES, ALTHOUGH SOMEWHAT AMBIGUOUS, SEEN IN ULTRAFILTRATION RATE, UREA CLEARANCE, AND DIALYSATE VOLUME OVER REGULAR CAPD. |
| 3. POLY(dl-LACTIDE GLYCOLIDE) MICROCAPSULES GROUP # 5 | ○ BLOOD GLUCOSE LEVELS SIGNIFICANTLY INCREASED WITH PUMP OVER REGULAR CAPD. |
| 4. ETHYLCELLULOSE MICROCAPSULES GROUP # 4 | ○ FUNCTIONAL AS A CONTROLLED RELEASE CONFIGURATION BOTH in-vitro AND in-viva |
| 5. COACERVATE AND DENATURED GELATIN MICROCAPSULES GROUP # 1 | ○ FUNCTIONAL AS A CONTROLLED RELEASE CONFIGURATION BOTH in-vitro AND in-viva<br><br>○ FUNCTIONAL AS A CONTROLLED RELEASE CONFIGURATION BOTH in-vitro AND in-viva |
| 6. ALGINATE MICROCAPSULES GROUP # 3 | ○ NON-FUNCTIONAL |

FIG. 18

PERITONEAL DIALYSIS METHOD

CROSS-REFERENCE TO RELATED APPLICATION

This is a continuation in part of application Ser. No. 876,941, filed June 20, 1986, abandoned Aug. 11, 1988 which disclosure is incorporated by reference.

BACKGROUND OF THE INVENTION

1. Field of the Invention

This invention relates to an improved method for conducting peritoneal dialysis, and especially to an improved method of performing continuous internal peritoneal dialysis for the maintenance of patients with inadequate kidney function.

2. Description of the Art

Patients with chronic renal failure and anephric patients require a replacement, in one form or another, for the functions normally performed by the kidneys. These include the maintenance of fluid and electrolyte balance, the excretion of nitrogenous and other bodily wastes, the elimination of foreign molecules not removed by other means, and the retention of desirable body components present in the blood, such as nutrients and proteins. For those patients who cannot obtain or cannot sustain a transplant kidney, the only practical solution is an artificial kidney process of some sort (i.e. hemodialysis).

A widely used method of dialysis is extracorporeal hemodialysis. Here the patient's blood is cleansed by passing it through an artificial kidney in an artificial kidney dialysis machine.

A semipermeable membrane is interposed between the patient's blood and a suitably formulated dialysis solution. According to conventional theory, water, electrolytes, and other relatively small molecules diffuse in the direction of the osmotic gradient, which is determined by the formulation of the dialysis fluid. The dialysis fluid is so formulated that by the conclusion of the dialysis process, excess water, foreign compounds and nitrogenous wastes have diffused into the dialysate fluid. Proteins and other large molecules have been retained on the blood side of the membrane, and electrolyte concentrations have equilibrated on both sides of the dialysis membrane at normal levels.

The process of water removal by diffusion, from the patient's blood across the membrane is called ultrafiltration.

Extracorporeal hemodialysis is generally required three times per week, each session requiring 4 to 5 hours in a dialysis center or at home. During dialysis, the patient is "tied" to the machine by venous and arterial blood lines which convey the blood to and from the artificial kidney. The activities which the patient can perform are limited while the patient is "tied" to the machine. Thus, the patient's life is seriously affected as his or her daily activities must be planned around these sessions.

The dialysis process can be performed either outside the body as noted above by removing the blood and pumping it across any of the well known artificial semipermeable membranes, or in the body (endocorporeally), by placing a dialysis fluid in contact with a natural semipermeable membrane such as the peritoneal membrane (peritoneum). The peritoneum, which defines the peritoneal cavity, is a membrane lining the abdomen and pelvic walls. It contains many small blood vessels and capillary beds which act as a natural semipermeable membrane. In both extracorporeal and endocorporeal hemodialysis, impurities, toxins, and water in the blood are removed by diffusion across a membrane, a cellulose membrane of an artificial kidney or a peritoneal membrane of a peritoneal cavity respectively.

There are two types of such dialysis which utilize the peritoneal membrane, intermittent peritoneal dialysis and continuous ambulatory peritoneal dialysis.

With intermittent peritoneal dialysis a dialysate, typically containing glucose as an osmotic agent, is infused into the patient's peritoneal cavity by means of tubing and a catheter.

The dialysate remains in the patient's peritoneal cavity for a time sufficient for blood waste-products and water to be removed by diffusion across the peritoneal membrane and into the dialysate. The waste-products and water-containing dialysate then are drained from the peritoneal cavity by means of a catheter and tubing and a fresh supply of dialysate may be infused. Intermittent peritoneal dialysis (IPD) utilizes extracorporeal pumps or other auxilliary equipment to which the patient is "tied" during dialysis. The patient must remain sedentary while "tied" to the equipment. Here also, the patient's activities are seriously impeded.

For several reasons, an internal, continuous ambulatory (equilibrium) peritoneal dialysis process (CAPD) has features which cause it to be preferred by many patients. First, the patient can be ambulatory when an internal membrane is used because no pumping mechanism is needed and the key element required, the dialysis membrane, goes wherever the patient goes, i.e. the patient is not tied to a machine.

The patient need be sedentary only for the time required to drain and infuse dialysate from and into the peritoneal cavity.

In an intermittent external hemodialysis process, the high flow rates and rapid fluid or solute transfers involved tend to leave the patient exhausted after the dialysis, and higher levels of toxic wastes accumulate between dialyses. Both of these factors negatively affect the patient's sense of well being. The external hemodialysis process also requires repeated blood access which tends to cause vascular damage, wherein an internal peritoneal dialysis process does not require blood access.

Continuous dialysis using an equilibrium approach has been employed as a substitute for normal kidney function in thousands of patients. In a typical process, two liters of a suitably formulated dialysis solution, such as INPERSOL ® Peritoneal Dialysis Solution, is infused into the peritoneal cavity through a permanently implanted peritoneal access catheter in the patient's abdominal wall.

Typically, when the dialysis solution container is empty, it is not disconnected from the tubing leading into the patient's peritoneal cavity. Instead, the patient simply rolls up or folds the container and tucks it into his clothing. The peritoneal access is thereby sealed and the solution is allowed to equilibrate for 4 to 6 hours. At the end of this period, the peritoneal access is opened and the spent dialysate is drained from the peritoneal cavity, again typically directly into the folded container and then discarded. The patient if necessary, replaces the container with fresh dialysate. The entire process can be repeated on a continuous basis, day and night, for as long as the patient requires a substitute kidney.

A disadvantage of the foregoing process is that the equilibration process occurs at different rates for different materials, depending upon molecular size, charge, and other factors Water, for example, equilibrates rapidly, flowing across the membrane and diluting the dialysis solution.

It has now been discovered that as water transfers across the membrane, it carries other small water-bound molecules with it. One such small molecule is urea, the principal nitrogenous metabolite produced by the body. Because of this phenomenon, urea transfer in the initial phase of the dialysis process has now been shown to be greater than can be accounted for by diffusion in response to an osmotic gradient.

However, once water equilibrates and the net transfer of water into the dialysis solution ceases, the urea is free to diffuse back across the membrane into the blood. Since this occurs fairly early in conventional continuous dialysis processes, it has now been shown that removal of small highly hydrated solutes is poorer in the continuous dialysis processes than in conventional intermittent processes in which an osmotic gradient is maintained and water transfer across the membrane occurs throughout the dialysis period.

Another disadvantage has already been mentioned. A substantial volume of excess water is removed from the body in the dialysis process, which is desirable. However, because the water transfers rapidly and equilibrates early in an equilibrium dialysis process, the patient is burdened with carrying the original volume of dialysis solution plus that large volume of fluid in the peritoneal cavity for the entire dialysis period.

Yet another disadvantage with the conventional internal continuous process is that it generally requires 4 to 6 fluid exchanges per day. Although these exchanges do not require blood access, each exchange presents an opportunity for microbial contamination. When contamination occurs, it frequently results in peritonitis, which requires intensive medical management and can ruin the peritoneum as a dialysis membrane. By reducing the number of exchanges required, an improved method would reduce the opportunity for such contamination and complications.

In view of these recognized disadvantages, there is an ongoing effort to improve the continuous internal dialysis process to make it safer and more effective for the patient. Such an improved process would also desirably be applicable to the acute dialysis of patients in need of such treatment, such as those suffering from poisonings and drug overdoses.

As used herein, the term "continuous" as in continuous ambulatory peritoneal dialysis (CAPD) means a substantially constant presence of a dialysate fluid which is maintained within a patient by a process of infusion, a definitive dwell time for the dialysis fluid within the peritoneal cavity and thereafter substantial removal of the modified dialysis composition. For maintenance of the patient, this procedure then requires repetition of the above noted steps. This is contrasted to use of the term "continual" in which the dialysis solution is added (or removed) in an ongoing manner, perhaps by utilization of a circulation loop, or by an infusion pump such as the Abbott/Parker Life Care 1500 ® ambulatory microinfuser, with resulting drainage of the fluid at a predetermined volume or osmolality concentration.

It has previously been suggested, in UK patent application No. 2,132,914, Milner et. al., that peritoneal dialysis solutions add glucose polymers to increase their osmotic pressure The adjustment of the osmolarity being within the needs of the clinician. Milner et. al. utilize a CAPD method with a single release of the osmotic agent(s) into the peritoneal cavity for each complete treatment, and since repeated treatments are used, the osmotic agent is released intermittently. A single infusion is administered with all of the active agent present and available at one time. The dialysis fluid is allowed to equilibrate with the body fluids, using a dwell time of about 4-6 hours.

PCT application WO 85/0555, Pearson et al. relates to the addition of monophosphoryl lipid A to a peritonial dialysis solution to suppress symptoms of peritonitis. Pearson et al. also utilizes the conventional CAPD methods for administration of the supplemented dialysis fluid.

Siefter et al., U.S. Pat. No. 3,911,915, issued Oct. 14, 1975 relates to a method of nourishment using maltose. An intraperitoneal (I.P.) injection of the iso-osmotic solution of maltose is administered five times daily. No fluid is removed from the peritoneal cavity. Siefter et al. thus teaches a method of parenteral nutrition. It does not teach, nor suggest the continual release of an osmotic agent into the cavity, nor maintenance of a substantially constant osmolarity of the dialysate solution.

Nolph et al. European patent application, 0,089,135 relates to the use of particulate sorbents in peritoneal dialysis solutions. Nolph et al., like the others defer to the prior art in so far as the formulations and methods of dialysis are concerned. Nolph et al. also observe that ultrafiltration occurs in their experimental system, and because of the design of that method the osmolarity of the dialysate must decrease with time as does the ultrafiltration rate. These decreases are precisely what the invention disclosed herein is meant to correct.

SUMMARY OF THE INVENTION

The CAPD process of the present invention differs from other current peritoneal dialysis techniques. This invention provides for an improved method of dialysis with decreased total volume of dialysis solution used and increases in efficacy parameters such as ultrafiltration rate, urea clearance rate and dialysate volume as compared to conventional techniques.

In the method of this invention, fluid communication through the peritoneal membrane into the peritoneal cavity is established. An initial volume of an aqueous peritoneal dialysis composition containing an osmotic agent is instilled into the peritoneal cavity through the fluid communication. The dialysis composition contains an amount of dissolved osmotic agent (i) that is insufficient to adequately dialyze the patient during a predetermined time period of dialysis treatment, but (ii) that is present at an osmolarity that is greater than the osmolarity of the body fluids in contact with the membrane, such that an osmolarity gradient is created across the membrane between the composition and the body fluids by means of which gradient a flux of water and solute enters the composition. This is followed by continually releasing a further dissolved osmotic agent into the instilled dialysis composition to form a modified dialysis composition. The further osmotic agent is released in an amount sufficient to maintain a substantially constant osmolarity gradient between the modified dialysis composition and the body fluids such that the water and solute flux continue to enter into the modified dialysis composition during the predetermined dialysis time period. The resulting modified dialysis composition is substantially removed from the peritoneal cavity at the end of the time period.

The effect of the method of this invention is to use the water removed by the body to make additional dialysis composition in situ which minimizes the volume of composition which must be initially instilled. The maintenance of the osmotic gradient substantially prevents ultrafiltration efficiency from dropping due to dilution of the dialysis solution.

In one embodiment of this invention, the initial volume or bolus of the dialysis composition is formulated to contain all of the osmotic agent required for the entire dialysis period. A large proportion of the osmotic agent is incorporated into a controlled release form and is consequently not dissolved in the composition and immediately useful for dialysis. The sequestered osmotic agent provides continual and gradual release of the osmotic agent into the instilled and modified dialysis composition over a period of predetermined time. The osmotic agent maintains the gradient at a level which assures continuing water and solute flux into the modified dialysis fluid, preferably maintaining a concentration of the osmotic agent in the modified dialysis solution of from about 300 to about 500 mOsm/L.

In another embodiment, an initial volume of conventional aqueous dialysis solution is instilled as described above but the continually released osmotic agent is instilled into the modified composition in a controlled manner from a reservoir which is external to the peritoneal cavity by a pumping means also external to the cavity. The rate of release is selected to maintain a substantially constant osmotic gradient across the peritoneum. This is preferably accomplished by maintaining an osmolarity of the dialysis solution of from about 300 to about 500 mOsm/L. The concentrated solution containing the osmotic agent is preferably from about 50 percent w/v to about 90 percent w/v.

BRIEF DESCRIPTION OF THE DRAWINGS

The various features and advantages of the invention will appear from a description of the figures and their embodiments of the invention herein. More specifically FIG. 12 compares in tabular form the various parameters for conventional CAPD with those for the controlled release CAPD method of the present invention. FIG. 13 illustrates the Blood Glucose Concentration in animals treated with conventional CAPD methods and animals treated with the "pump" controlled release method of the present invention.

FIG. 1 shows a plot of Ultrafiltration [UF; in millimeters per minute (ml/min)] and of Volume [Volume; in ml] versus Time [in minutes (min)].

FIG. 2 shows a plot of Urea Nitrogen Concentration [in milligrams per decaliter (mg/dl)] for both Blood and Dialysate versus Time [in minutes (min.)].

FIG. 3 shows a plot of Osmolality [in milliosmoles per kilogram (mOsm/kg)] for both Dialysate and Serum Osmolality versus Time [in minutes,(min.)].

FIG. 4 shows a plot of Dextrose Concentration [in milligrams per decaliter (mg/dl)] versus Time [in minutes (min.)].

FIG. 5 shows a plot from Example 3 of the present invention of Urea Clearance [in milligrams per kilogram per min (mg/kg/min)] versus Time [in hours].

FIG. 6 shows a plot from Example 3 of Ultrafiltration Rate [in microliter per kilogram per min ) versus Time [in hours].

FIG. 7 shows a plot from Example 3 of Dialysate Volume [in milliliters per kilogram (ml/kg)] versus Time [in hours].

FIG. 8 shows a plot from Example 4 of Intraperitoneal (I.P.) Volume [in milliliters (ml)] versus Time [in hours].

FIG. 9 shows a plot from Example 4 of Ultrafiltration Rate [in milliliters per min (ml/min)] versus Time [in hours].

FIG. 10 shows a plot for Example 4 of Total I.P. Urea Clearance [in milligrams (mg)] versus Time [in hours].

FIG. 11 shows a plot for Example 4 of Total I.P. Urea Clearance [in milligrams (mg)] versus Time [in minutes (min.)].

FIG. 12 shows a Comparison of Efficacy Parameters for Regular CAPD versus those for the Controlled Release Formulations of Example 4.

FIG. 13 shows a plot for Example 4 of Blood Glucose Concentration [in milligrams per decaliter (mg/dl)] for conventional CAPD and the Controlled Release Formulations of this invention versus Time [in hours].

FIG. 14 shows a plot for Example 4 of Ultrafiltration Rate Comparisons [in milliliters per minute (ml/min)] of Three Microcapsule Systems versus Time [in hours].

FIG. 15 shows a plot for Example 4 of Pump and Bead Dialysate Volumes [in milliliters (ml)] versus Time [in hours].

FIG. 16 shows a plot for Example 4 of microcapsules (Formula 2-A) for Urea Concentration [in milligrams per decaliter (mg/dl)] and Dialysate Volume [in milliliters (ml)] versus Time [in hours].

FIG. 18 presents a Summary of Findings for Examples 3 and 4 as Controlled Release Peritoneal Dialysis studies.

DETAILED DESCRIPTION OF THE INVENTION

Figure 1:
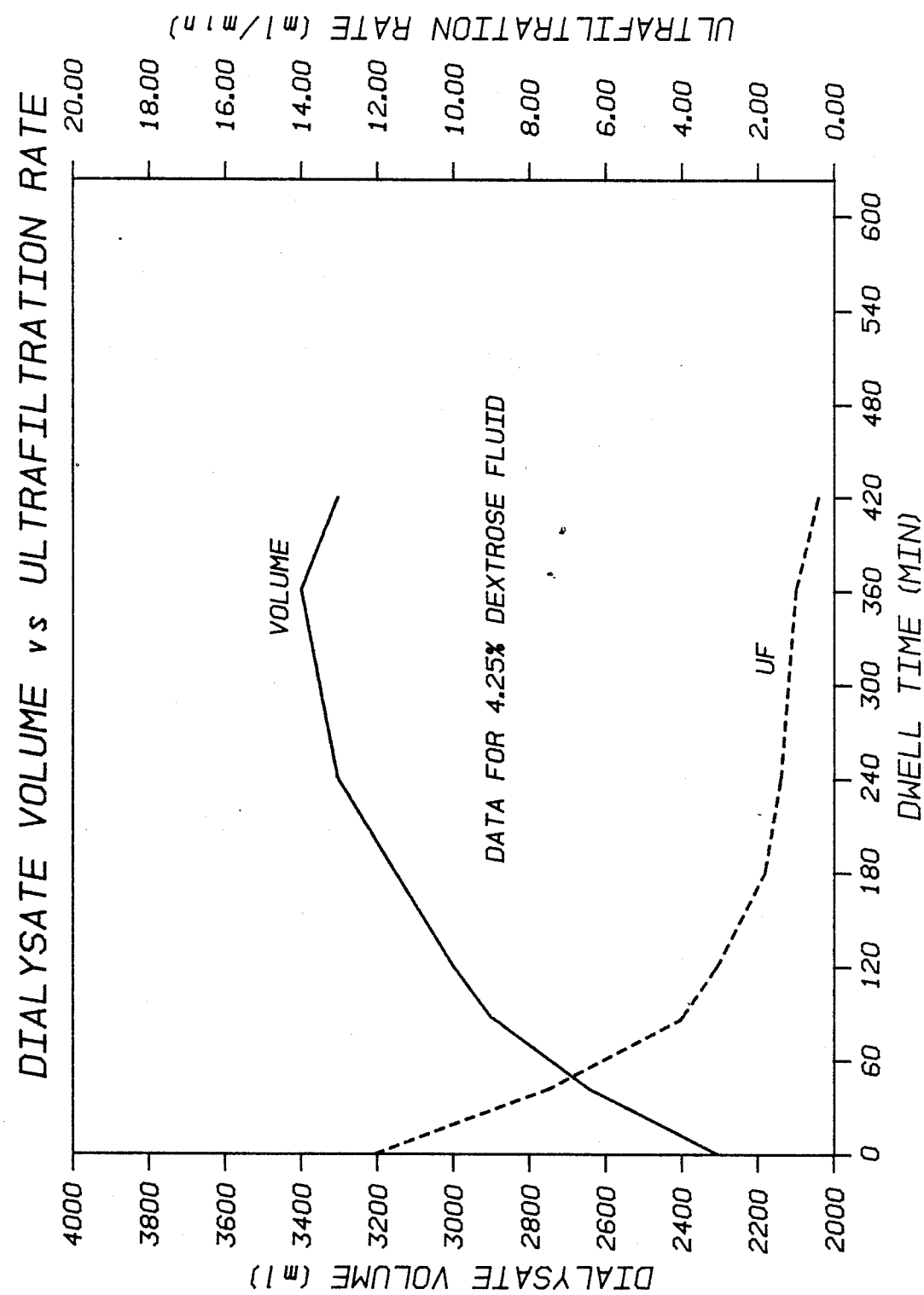
FIGS. 1 through 4 are copies of graphs taken from Nolph, K.D., Peritoneal Dialysis, 2nd Edition, Nijhoff, Boston, 1985, and illustrate results typically obtained with standard CAPD methods
Figure 2:
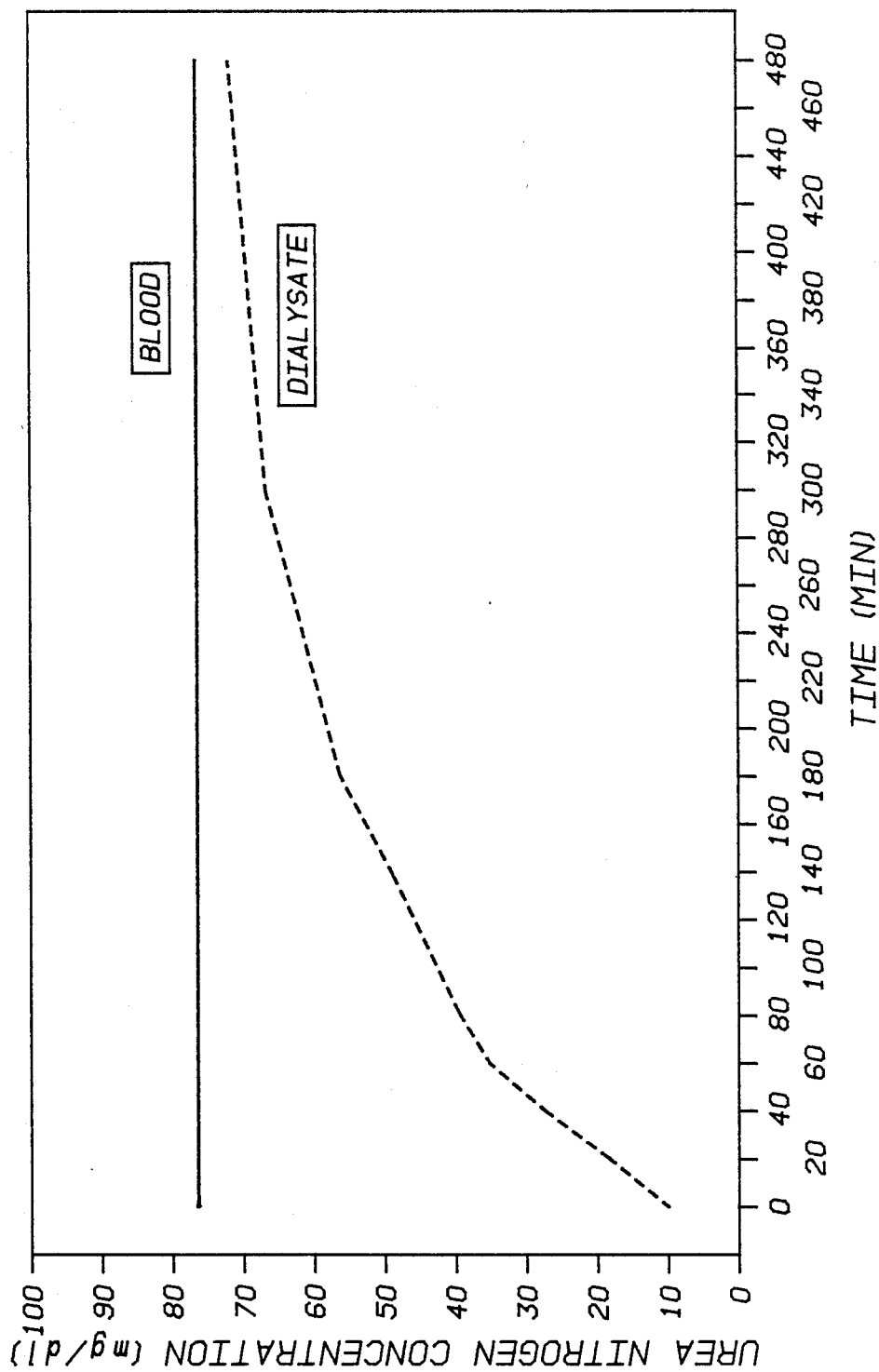
Figure 3:
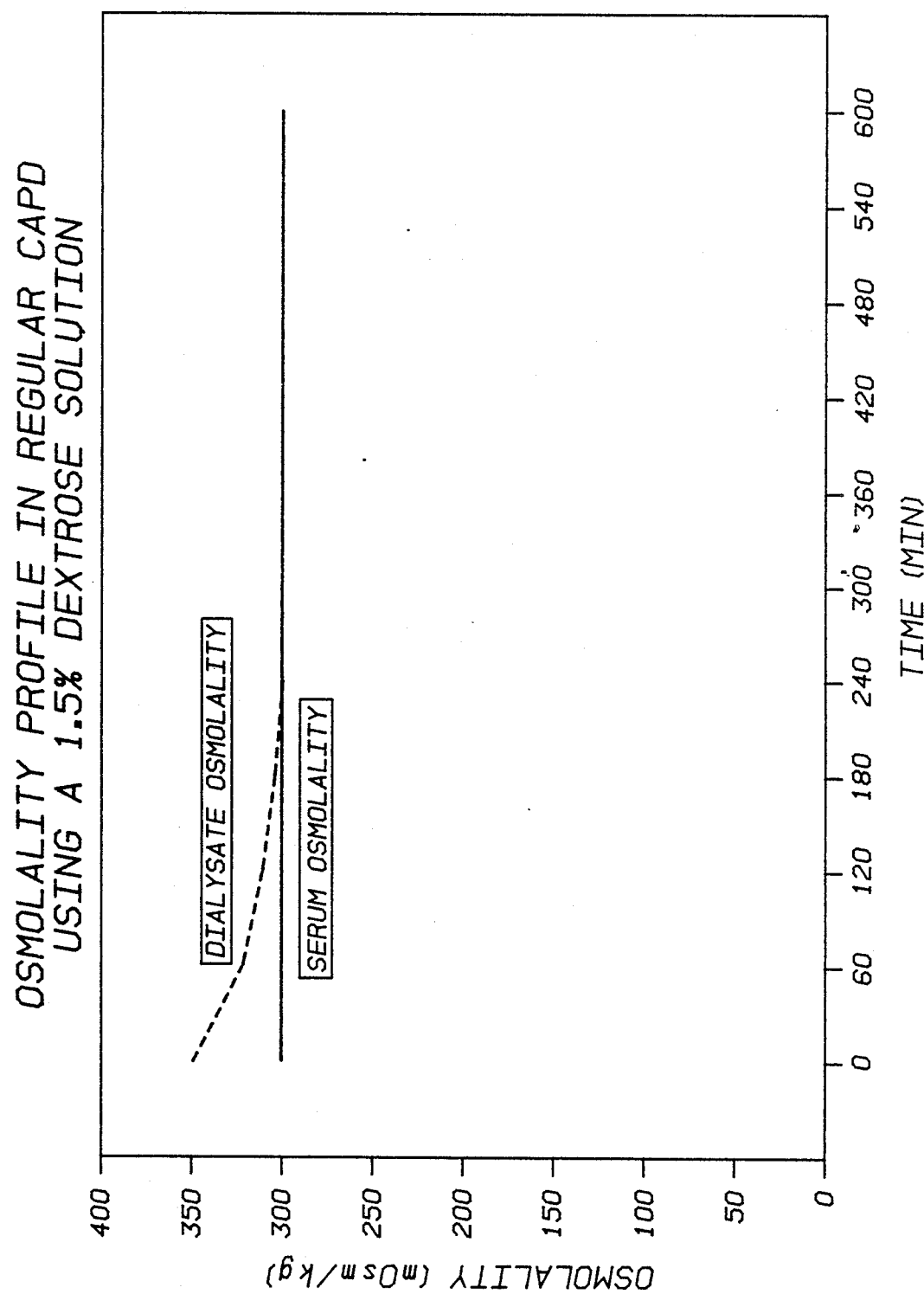
Figure 4:
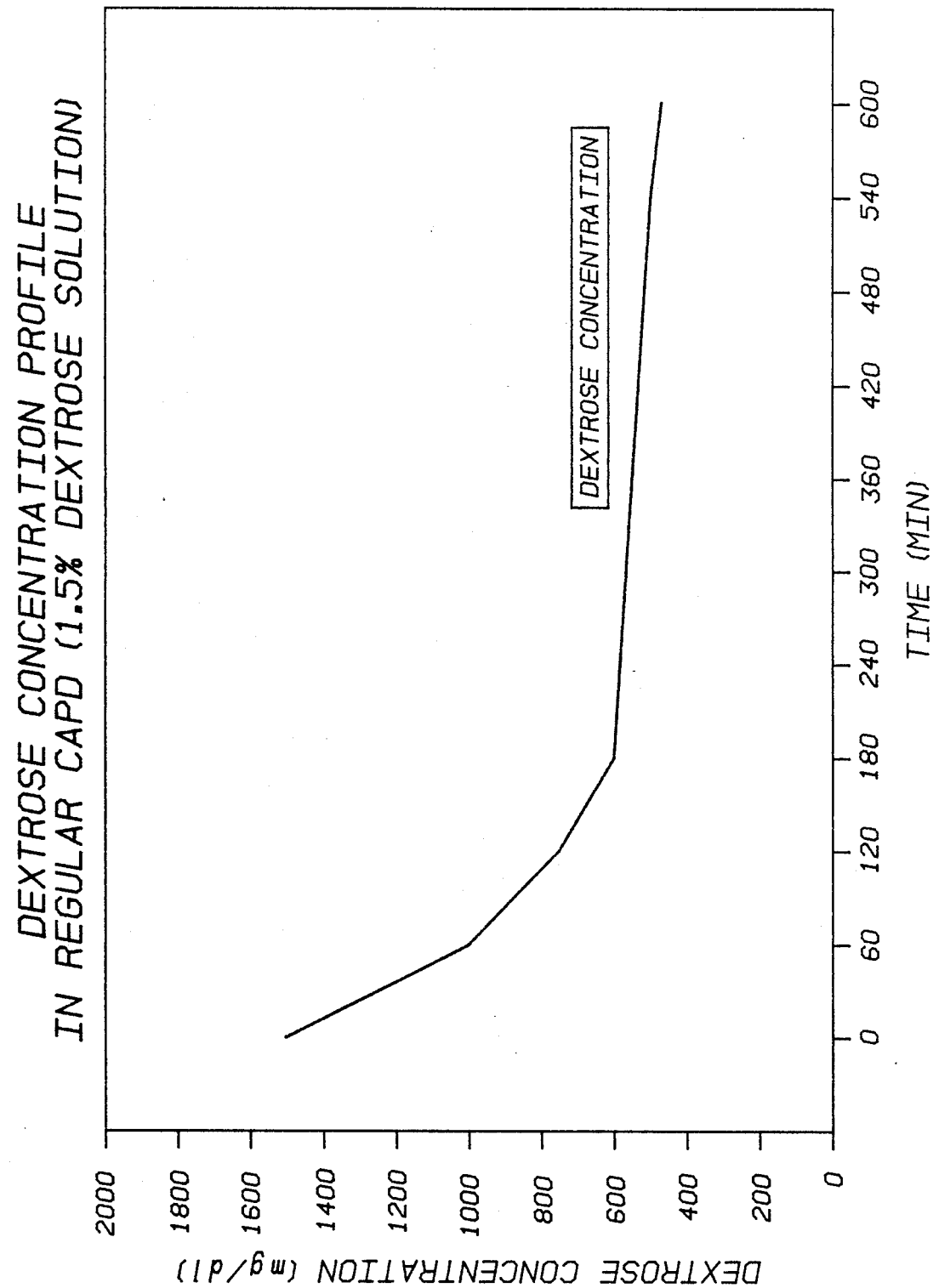

This invention provides an improved method for conducting peritoneal dialysis. In the method of this invention, a fluid communication through the peritoneal membrane into the peritoneal cavity of the patient is established. A catheter as is usually utilized in a CAPD method is typically employed and is well known in the art. A surgically implanted indwelling catheter with a suitable connecting means for accepting the dialysis composition is typically employed.

An initial volume (or bolus) of an aqueous dialysis composition is instilled into the peritoneal cavity through the fluid communication The dialysis composition contains an amount of dissolved osmotic agent
  (i) that is insufficient to adequately dialyze the patient during a predetermined time period of dialysis treatment, but
  (ii) that is present at an osmolarity that is greater than the osmolarity of the body fluids in contact with the membrane,
such that an osmolarity gradient is created across the membrane between the composition and the body fluids by means of which gradient a flux of water and solute enters the composition.

Following this initial fluid introduction, further dissolved osmotic agent is continually released into the instilled dialysis composition to form a modified dialysis composition. The further osmotic agent is released in an amount sufficient to maintain a substantially constant osmolarity gradient between the modified dialysis composition and the body fluids such that the water and solute flux continue to enter into the modified dialysis composition during the predetermined dialysis time period. The modified dialysis composition is substantially removed from the peritoneal cavity at the end of the predetermined time period. The previous steps are repeated seriatim to provide discrete dialysis treatments for as long as the patient is in need of such treatment.

Alternatively, the process of this invention can be practiced in a true continual manner, so that the dialysis period is extended indefinitely, as in the kidney. In this true continual process, the spent modified dialysate composition from the peritoneal cavity is removed concurrently with continuation of the dialysis process by draining the spent dialysate through a second similarly formed fluid communication with the peritoneal cavity, while continuing release of osmotic agent into the peritoneal cavity through the first fluid communication.

Preferably the initial bolus has a solute concentration, including dissolved osmotic agent concentration of from about 300 milliOsmoles per liter (mOsm/L) to about 500 mOsm/L. Preferably the predetermined time period is from about 6 to about 24 hours.

Thus, according to the present invention, the initially instilled volume does not contain an amount of osmotic agent that would be needed for the patient to be adequately dialyzed during the predetermined treatment time. Amounts of osmotic agents that are adequate are well known in the art and are readily calculatable for a particular patient. In preferred practice, the amount of osmotic agent utilized is at most about 50 ml to about 500 ml, and more preferably about 100 ml to about 250 ml as compared to conventional volumes of about two liters.

The present invention thus differs significantly from the previously described CAPD methods. For example, Milner et al. utilizes a single instillation of the osmotic agent into the peritoneal cavity. That method is to be contrasted with the present invention in which an osmotic agent(s) is continually released into the peritoneal cavity. Here, an initial volume (a bolus) that cannot adequately dialyze the patient during the treatment time is instilled, which Milner et al. do not teach. Second, the continual release of the osmotic agent into the cavity maintains a substantially constant osmolarity in the dialysis fluid, a feature also not taught by Milner et al.

The efficiency of the dialysis composition is substantially maintained throughout the dialysis treatment in the present method, whereas the osmolarity in the dialysis solution drops over time as water diffuses into the dialysis solution without a compensating osmotic agent.

The invention herein is also to be contrasted with the previous conventional techniques that do not require a continual addition or release of a dissolved osmotic agent into the dialysis composition once it is instilled into the peritoneal cavity Pearson et al do not teach that dissolved osmotic agent(s) is constantly released into the dialysis composition, either by dissolution of microencapsulated osmotic agent or by influx from outside the peritoneal cavity The continual release of the dissolved osmotic agent of the present invention produces an osmolarity gradient such that a constant water and solute flux is maintained during the predetermined dialysis period.

The conventional techniques used by Siefter et al., Pearsons et al., or Milner et al. consequently all instill a solution into the peritoneal cavity, have a dwell time of about 4–6 hours before removing the dialysis solution, (or do not remove the solution as in Siefter et al.), and as such do not maintain the osmolarity gradient of the dialysis solution constant While Siefter et al. suggest that maltose can be used as a replacement for dextrose in cases of peritoneal dialysis or poisoning, the specific factors as needed to practice the disclosed invention herein are not present. Most importantly Siefter et al. utilize an iso-osmotic solution whereas the invention as claimed requires a gradient to be established between the peritoneal dialysis composition and the body fluids. It is also well known in the art that maltose can be substituted for dextrose at twice the maltose concentration.

The volume of aqueous dialysis composition initially instilled in the peritoneal cavity depends upon the total content of osmotic agent and other osmotically active solutes and the characteristics of the controlled release osmotic agent formulation, as well as the size of the patient, the level of any residual kidney function, the diet and metabolic characteristics of the patient, and other similar factors familiar to the nephrologist experienced in the practice of conventional peritoneal dialysis.

Similarly, selection of other components in the dialysis composition, such as amino acids, antibiotics, proteins and/or electrolytes, also depends on these latter factors. Preferably, a range of various formulations may be employed, at the discretion of the nephrologist. Beyond the volume and osmolarity limits described herein, and the design of the desired controlled release system, the formulation and compounding of such solutions is within the routine skill of the hospital pharmacist or pharmaceutical chemist and of itself forms only a part of the present invention.

To create osmotic pressure which is necessary to cause dialysis, the dialysis composition of any embodiment herein must contain an osmotic agent, generally dextrose. The concentration of an osmotic agent in a solution which is required to produce a given osmotic pressure is directly related to its molecular weight. The osmolarity of a solution is normally calculated by reference to the number of molecules in the solution. It would therefore be expected that if dextrose were replaced by a compound having twice the molecular weight of dextrose, i.e. maltose, than twice the concentration of maltose would be needed. For example, if a 5% dextrose solution is used, a 10% concentration of maltose would be needed to have equivalent osmolarity.

"Osmotic agent" as used herein is a compound(s) which exerts an osmotic force in solution and is taught for use in peritoneal dialysis primarily as an osmotic agent to draw excess water out of the body. While in absolute terms many of these compounds are not ideal osmotic agents in the sense that they are entirely nondiffusible across the peritoneum, they are relatively so and are thus usable in maintaining an osmotic gradient as desired.

Exemplary compounds useful as an osmotic agent include those commonly used in peritoneal dialysis, such as dextrose and other sugars, as well as less common materials taught to be suitable for peritoneal dialysis, such as sugar polymers, synthetic non-calorigenic materials, such as saccharin, cyclamate, and aspartylphenylalanine methyl ester, commonly referred to as aspartame; amino acids, alpha-keto analogs of the amino acids and alpha-keto acid salts of the amino acids, albumin and other plasma proteins; phosphatides; and the like.

Preferably, the osmotic agent employed in the practice of this invention is a relatively large or charged molecule which by virtue of its size or its charge (or both) is incapable of crossing the peritoneum, and thus is not absorbed by the body to any significant degree. However, the choice of a suitable osmotic agent is a simple matter for the practitioner of ordinary skill, and of itself forms no part of the present invention. It is to be understood that other relatively nondiffusible solutes in the dialysis solution will also exert some osmotic pressure; however, these solutes are incorporated primarily as electrolytes, and the like, and not for their osmotic effect. It is also contemplated that a combination of one or more osmotic agents may be used together within the scope of this invention.

The term "amino acid" herein is intended to include the common alpha-amino acids glycine, alanine, serine, cysteine, aspartic acid, glutamine, glutamic acid, hydroxylysine, leucine, isoleucine, asparagine, tyrosine, tryptophan, histidine, phenylalanine, cystine, proline, hydroxyproline, threonine, lysine, methionine, valine and taurine. The terms "alpha-keto analogs of amino acids or "alpha-keto acids" are intended to include compounds corresponding in structure to the foregoing amino acids but in which the alpha-amino moiety is replaced by an alpha-ketone moiety In one embodiment of this invention, the initial volume of dialysis composition, preferably from about 0.1 to about 1.0 liters, is formulated to contain all of the osmotic agent required for the entire dialysis period, a large proportion of the osmotic agent as dissolved hereinafter, being incorporated in the composition in controlled release form. This fluid is instilled into the peritoneal cavity.

The osmotic agent is sequestered in a material which provides continuous and gradual release and dissolution of the osmotic agent over a period of several hours. Throughout the dialysis period, as water transfers across the peritoneum and dilutes the modified composition or modified dialysate, the osmotic agent which is gradually released and dissolved maintains the osmotic gradient at a level which assures continuing water and solute flux into the dialysis fluid, preferably maintaining a concentration of dissolved, free osmotic agent in the modified dialysis composition of from about 300 mOsm/L to about 500 mOsm/L. At the point at which all of the osmotic agent has been released, the dialysis process can be repeated by substantially draining the spent modified composition (dialysate) from the peritoneal cavity and instilling a fresh volume of composition. For as long as the patient requires a continuing replacement of kidney function, this process can be repeated regularly thereafter.

In a variation of this embodiment, the total concentration of osmotic agent in a controlled release form can be instilled into the peritoneal cavity following an initial bolus injection of a conventional CAPD dialysis solution to form the dialysis composition. A conventional CAPD solution has an osmolarity of about 300 mOsml/L to about 500 mOsm/L. The process then continues as described above.

In this embodiment, from 50% to 99%, preferably 75% to 95% of the osmotic agent, is sequestered in a nontoxic, physiologically compatible material which gradually releases the sequestered osmotic agent into solution in the peritoneal cavity. Preferably, the sequestering material gradually loses its structural integrity upon prolonged exposure to an aqueous environment, so that problems with granulomatous foreign body reactions are avoided. For this reason it is also desirable that the sequestered material be incorporated in the dialysis composition in the form of micronized particles, such as microcapsules or microspheres, which will not provoke a peritoneal or immune reaction.

The matrix is preferably designed to achieve a preferred zero order release of the granules in a predetermined time period, preferably from about 6 to about 12 hours. A matrix diffusion system, where the drug is uniformly dissolved or dispersed, may also be used which has a first-order release behavior (rate) release with a continuously diminishing release rate may also be used.

The polymer erodes by hydrolysis or enzymatic cleavage, and the like, the drug is released to the surrounding environment. The terms "bioerodible" and "biodegradable" are used herein as interchangeable. "Bioerodible" is usually reserved for systems where the polymer erosion occurs in a time scale similar to that of the drug release The erosion process has a direct effect on the drug release.

The erosion/degradation products may have different degrees of toxicity To reduce this toxicity preferably used, but not limited thereto, are the poly (lactic acid), poly (glycolic acid), and lactic/glycolic acid copolymers which hydrolyze to natural metabolites; cellulose and cellulose derivatives; the polyorthoesters, polycarpolactone, polyaminoacids, polyanhydrides and half esters of methyl vinyl ether-maleic anhydride copolymers; the natural polymers such as polysaccharides and the synthetic polymers such as polylysine, polyglutamic acid, polyphosphazens, copolymers of vinylpyrrolidone, and copolymers of 2-hydroxypropylmethacrylamide, and like materials used in this art.

Since the osmotic agent is released and dissolved upon exposure to an aqueous environment, it may be necessary to formulate the dialysis solution in a two-part, dry-plusaqueous form. The resulting product can be provided in any convenient system for packaging a dry drug product with an aqueous vehicle. The two parts are combined at the point of use. One such system is the ADD-Vantage ® drug delivery system manufactured and sold by Abbott Laboratories, North Chicago, Ill., described in U.S. Pat. Nos., 4,614,267, issued 9/30/86 and 4,614,315, issued 9/30/86 the disclosures of which are incorporated herein by reference.

In another embodiment of the method of this invention, the osmotic agent is retained in dissolved concentrated fluid form in a container outside the body, and is gradually and continuously released into the peritoneal cavity in a controlled manner by pumping means in fluid communication with the peritoneal cavity. The concentrated fluid can be in the form of a solution, suspension, emulsion, or a combination thereof and is hereinafter referred to as an aqueous dialysis composition.

The rate of release of concentrated osmotic agent into the peritoneal cavity is selected to maintain a substantially constant osmotic gradient across the peritoneum in the face of the anticipated water transfer from the blood stream As with the previously described embodiment, this transfer is preferably accomplished by maintaining a dialysis solution osmolarity of from about 300 mOsm/L to about 500 mOsm/L. As a result, a substantially constant water and solute flux is maintained over the entire predetermined dialysis period.

In this latter embodiment the aqueous dialysis composition containing the osmotic agent is preferably a concentrated solution having an osmotic agent concentration of from about 50% weight/volume (w/v) to about 90% w/v, and most preferably about 70% w/v. Other solutes, such as calcium, magnesium, potassium, and the like, may be included in proportional concentrations.

By "pumping means" is meant any suitable means for automatic and controlled delivery of the appropriate quantity of osmotic agent-containing composition into the peritoneal cavity. This includes, for example, any of the small, battery powered, microprocessor-controlled wearable pumps used in the ambulatory administration of antibiotics and cancer chemotherapeutic agents, such as the Abbott/Parker Life Care 1500 ® ambulatory micro infuser system. Alternatively, a pressurized delivery container can be coupled with a rate limiting valve to provide controlled delivery of the solution without the need for batteries or other electronic mechanisms.

The pumping means must be capable of providing substantially continuous delivery of osmotic agent to the peritoneal cavity over a period of at least 6 hours, preferably at least 24 hours, and most preferably a week or more. With delivery periods of from 12 to 24 hours, a once- or twice-per-day dialysis treatment schedule can be employed. With delivery periods of 24 hours or more, a true continuous dialysis process can be employed which is only interrupted to change or replace the power supply for the pumping means and to replenish the supply of osmotic agent.

A surprising benefit of this invention is that longer infusion and dialysis periods actually require less osmotic agent, and thus expose the body to a smaller absorptive load, than shorter infusion periods. Thus, for example, the caloric load imposed by absorption of the osmotic agent dextrose from conventional dialysis fluid can be reduced by the practice of this invention.

In the latter embodiment it is also preferred to instill a small initial volume of conventional dialysis solution as aqueous peritoneal dialysis composition to facilitate wetting of the large peritoneal surface area. In general, an initial volume of from 0.1 to 0.5 liters, preferably 0.25 to 0.4 liters of dialysis solution is employed. Such conventional dialysis solutions typically contain about 1.5 to about 4.5 weight percent dissolved dextrose as osmotic agent, and when utilized at an above volume, contain an amount of dissolved osmotic agent that is insufficient to adequately dialyze a patient in the 6 to 24 hour dialysis treatment time period contemplated herein.

Following this initial volume, the concentrated solution is administered in a volume and of an osmotic agent concentration sufficient to maintain a solution osmolarity of from about 300 mOsm/L to about 500 mOsm/L, preferably from, about 315 mOsm/L to about 375 mOsm/L, most preferably 325 mOsm/L. Using dextrose as an osmotic agent in a 70 kg adult with a 250 mL initial solution volume, requires administration of the concentrated osmotic agent from about 2 to about 2.5 grams of dextrose, preferably about 2.1 to about 2.3 grams of dextrose, most preferably about 2.2 grams of dextrose per hour for a 12 hour dialysis period, or from about 1 to about 1 3 qrams of dextrose, preferably from about 1.05 to about 1 15 grams of dextrose, most preferably about 1.1 grams of dextrose per hour for a 24 hour dialysis period. With fluid of known osmotic agent concentration, corresponding concentrate solution volumes can be calculated. For a commonly available 70% dextrose solution, these dosages correspond to a total delivery of about 75 mL per day, which represents about 3.12 mL per hour, for a 12-hour dialysis period, or 37.5 mL per day, which represents about 1.55 mL per hour, for a 24-hour dialysis period.

In the practice of this invention, water is osmotically removed from the patient on a continuous basis. Therefore, it is important to provide for the satisfactory hydration of the patient by requiring oral or I.V. intake of ample amounts of fluids which facilitate water and electrolyte balance.

In CAPD practice, the osmolarity of the solution is selected at the onset of instillation and the gradient initially established then deteriorates over the dwell or period of dialysis treatment time. During this dwell period, in the prior art, the osmotic pressure of the dialysis solution causes a net flow of water from the body. At the same time, the osmotic agent gradually diffuses into the body under the influence of the concentration gradient between the dialysis solution and the body fluids. Because of the flow of water into the dialysis solution and the diffusion of osmotic agent out of the dialysis solution, the osmolarity of the dialysis solution in conventional CAPD drops over the course of the dwell period.

As ultrafiltration across the peritoneal membrane is a direct function of the osmotic gradient, the ultrafiltration efficiency of the conventional method worsens over the dwell time. In addition, because the osmotic agent is added all at once in soluble active form, the volume of dialysis fluid during the exchange must be relatively large to avoid an excessively high osmolarity which would damage the cells lining the membrane This large volume is then increased by the additional volume of water supplied from the body by ultrafiltration thereby distending the cavity by the time the dwell period is over.

It has now been found that the removal of small, highly hydrated solutes, such as urea is poorer in a continuous dialysis process than in conventional intermittent processes in which the osmotic gradient is maintained. By the method of the present invention urea transfer in the initial phase of the dialysis process is unexpectedly shown to be greater than can be accounted for by diffusion in response to the gradient.

In conventional CAPD, once the water equilibrates and net transfer into the dialysis solution ceases, the urea is free to diffuse back across the membrane into the blood. The method of this invention maintains a constant osmotic gradient thereby preventing equilibrium in fluid volume, ultrafiltration rate, dialysis urea clearance and dextrose concentration.

The majority of ultrafiltration and waste product clearance during conventional CAPD occurs within the first 60-120 minutes of a regular CAPD fluid exchange. FIGS. 1-4 illustrate the rapidity at which substantial equilibrium is achieved during conventional techniques. The usual CAPD 30 regime uses 1-2 liters of Inpersol® 2.5% (or equivalent) instilled intraperitoneally for about four hours, at which time, a fluid exchange with fresh dialysate is accomplished. Other dialysis fluids (1.5% and 4.25%) are available to achieve lower or higher, respectively, ultrafiltration rates as desired by the clinician.

The conventional CAPD procedure, while possessing the advantage of allowing free movement of the patient, has the disadvantage of being time consuming (exchanges must be made every four hours or so) and, more importantly, is subject to the risk of causing infectious peritonitis. The method of this invention permits free movement by the patient with a decreased volume of dialysate which needs to be instilled as well as a decreased total volume of spent modified dialysate composition in the peritoneal cavity. Controlled release of an osmotic agent results in a demonstrable increase in efficacy of the dialysis process over regular or conventional dialysis processes.

The following examples clearly show significant improvements in the various parameters monitored in in vivo experiments. The improved method of performing continuous peritoneal dialysis disclosed herein provides for greater patient comfort, by reducing the number of required exchanges and therefore a lessening of the opportunity for microbial contamination, as well as the advantages of decreased volume of fluids enumerated above.

Industrial Applicability

The practice of this invention is further illustrated by the following examples:

EXAMPLE 1

A male rabbit weighing 2-3 kg was prepared for experimentation with light inhalation anesthesia. The animal was restrained on a typical restraining board. A micropump containing 50% dextrose solution was calibrated to deliver 1.09 grams dextrose (2.18 mL) per hour and connected with medical grade tubing to an intraperitoneal site within the rabbit. A 50 ml aliquot of conventional 4.25% dextrose peritoneal dialysis fluid was added to the peritoneal space and the infusion pump was allowed to deliver the programmed quantity of dextrose over a period of 8 hours. An intravenous saline infusion of 4 mL normal saline per kg per hour was administered concurrently to prevent dehydration and electrolyte derangement within the animal. At hourly intervals, the volume of ultrafiltrate within the peritoneum and the dialysate urea $N_2$ (UN) concentration were measured by standard techniques. The blood urea nitrogen (BUN) was measured before and after the experimental procedure by standard techniques. The results are as indicated in Table 1 below. It is clear from these results that the dialysate UN exceeded the BUN, indicating that the method of this invention resulted in improved efficiency in the dialysis procedure.

TABLE 1

| Time | Controlled Osmotic Agent Infusion | |
|---|---|---|
| | Dialysate Volume | Dialysate Urea Nitrogen |
| | Starting BUN: 22 mg/dL | |
| 0 | 240 mL | — |
| 1 hr. | 364 | 9.4 mg/dL |
| 2 | 498 | 19 |
| 3 | 562 | 26 |
| 4 | 414 | 38 |
| 5 | 489 | 41 |
| 6 | 192 | 46 |
| 7 | 678 | 45 |
| 8 | 483 | 40 |
| Ending BUN: 26 mg/dL | | |

EXAMPLE 2

Studies similar to those of Example 1 were conducted in additional rabbits. Each received an initial infusion (time zero) of Inpersol® 2.5%, which is a commercially available dialysis solution containing balanced electrolytes for peritoneal dialysis and 2.5% dextrose as an osmotic agent. Thereafter, two animals were treated with concentrated dextrose infusion in the manner of Example 1 using 20% and 50% dextrose, respectively; the third and fourth animals received an infusion of a dialysis composition containing insolubilized sequestered dextrose in the form of beads. Intraperitoneal volume, dialysate glucose, blood glucose, dialysate urea concentration, and blood urea concentration were measured on each animal. In addition, total intraperitoneal urea content was determined from the intraperitoneal volume and dialysate urea concentration.

In the third animal, the dextrose beads were formed using a combination of hydroxypropylmethyl-cellulose phthalate (HPMCP) and ethyl cellulose as the insolubilizing sequestering agent. The HPMCP remains intact at a pH value of about 5.5 or below, but dissolves at a pH value higher than 5.5. This allows the dextrose to remain sequestered prior to use, but permits release and dissolution of the dextrose into the composition at the pH value of the body and modified dialysis composition. In the fourth animal, the beads were formed using a polylactic acid-polyglycollic acid copolymer as the sequestering agent. Results are shown in Table 2, below.

TABLE 2

| Additional Treatment | Measurement | Hours after start | | | | | |
|---|---|---|---|---|---|---|---|
| | | 0 | 1 | 2 | 3 | 4 | 6 |
| Pump, D-20-W | IP Volume | 120 | 164 | 171 | 661 | 262 | 332 |
| 2 mL/hr | Dial. Gluc. (mg/dL) | 2500 | 2064 | 725 | 602 | 402 | 410 |
| + | Blood Gluc. (mg/dL) | 144 | 213 | — | 150 | — | 161 |
| IV Saline | Dial. Urea (mg/dL) | 0 | 8.6 | 10.9 | 11.9 | 13.0 | 13.7 |
| 30 mL/hr | Total IP Urea (mg) | 0 | 14.1 | 18.6 | 78.7 | 34.0 | 45.5 |
| | Blood Urea (mg/dL) | 12.1 | 11.8 | — | 12.6 | — | 14.4 |
| Pump, D-50-W | IP Volume | 112 | 170 | 252 | 415 | 213 | 386 |

TABLE 2-continued

| Additional Treatment | Measurement | Hours after start | | | | | |
|---|---|---|---|---|---|---|---|
| | | 0 | 1 | 2 | 3 | 4 | 6 |
| 2 mL/hr | Dial. Gluc. (mg/dL) | 2500 | 1619 | 1111 | 1208 | 857 | 748 |
| + | Blood Gluc. (mg/dL) | 135 | 225 | — | 228 | — | 202 |
| IV Saline | Dial. Urea (mg/dL) | 0 | 10.3 | 15.7 | 16.8 | 18.0 | 17.1 |
| 30 mL/hr | Total IP Urea (mg) | 0 | 17.5 | 39.6 | 69.7 | 38.3 | 66.0 |
| | Blood Urea (mg/dL) | 20.8 | 19.5 | — | 18.3 | — | 17.4 |
| Beads | IP Volume | 116 | 344 | 258 | 349 | 965 | 332 |
| 544 mg/kg | Dial. Gluc. (mg/dL) | 2500 | 1097 | 852 | 649 | 347 | 169 |
| + | Blood Gluc. (mg/dL) | 126 | 186 | — | 182 | — | 157 |
| IV Saline | Dial. Urea (mg/dL) | 0 | 10.3 | 14.2 | 15.8 | 15.8 | 16.6 |
| 30 mL/hr | Total IP Urea (mg) | 0 | 35.4 | 36.6 | 55.1 | 152.5 | 55.1 |
| | Blood Urea (mg/dL) | 17.0 | 15.7 | — | 17.1 | — | 16.4 |
| Beads | IP Volume | 106 | 142 | 350 | 302 | 265 | 339 |
| 1.22 g/kg | Dial. Gluc. (mg/dL) | 2500 | 705 | 817 | 611 | 352 | 188 |
| + | Blood Gluc. (mg/dL) | 110 | 154 | — | 157 | — | 122 |
| IV Saline | Dial. Urea (mg/dL) | 0 | 7.8 | 12.0 | 12.8 | 13.0 | 13.1 |
| 17 mL/hr | Total IP Urea (mg) | 0 | 11.1 | 42.0 | 38.7 | 34.5 | 44.4 |
| | Blood Urea (mg/dL) | 15.2 | 14.6 | — | 14.2 | — | 12.6 |

Examples 3 and 4 both demonstrate the controlled delivery of dextrose as disclosed and taught by this invention. In two studies run concurrently, on control animals, various efficacy parameters such as ultrafiltration rate, clearance rate, blood and dialysis glucose levels, and the like, were measured for both the "microencapsulation" and "pump" embodiments.

The procedure utilized in Example 3 can be described as follows:

EXAMPLE 3

Animal: Albino rabbits weighing 3.8-5.0 Kg
Pump: Abbott LifeCare 1500 Micropump ®
Primary Volume: 50 ml/Kg/hr of 50 percent dextrose solution over eight hours
Hydration: I.V. saline, 5 ml/Kg/hr
Experiment duration: Eight hours
Anesthesia: Light (hexabarbital or pentothal, as needed)

The procedure utilized in Example 4 can be described as follows:

EXAMPLE 4

Animal: Albino rabbits weighing 2.0-3.0 Kg
Pump: Abbott/Parker 1500 Micropump ®
Primary Volume: 40 ml/Kg of Inpersol ® 2 5%
Controlled Release: 2 ml/hour of 70 percent dextrose solution
Hydration: Saline I.V. 30 ml/hour
Experiment duration: Six hours
Anesthesia: None In both Examples 3 and 4, the control animals received only a bolus primary instillation. In the Example 3, this primary volume was 40 ml/Kg of Inpersol ® 2 5%. In the Example 4 the primary volume was 50 ml/Kg of Inpersol ® 4.25%. These two arrays of differing primary volumes and concentrations of dextrose encompass the optimum conditions of volume and concentration.

The initial animal studies were performed in order to develop basic methodologies, analytical procedures, and to determine optimum delivery rates for the controlled release of dextrose. In Example 3, dextrose was delivered through a subcutaneous implanted catheter to the peritoneal cavity, with the pump secured on the back of the restrained animal. In Example 3, the catheter ran from the pump on a stand to the peritoneal cavity of a restrained and lightly anesthetized animal. In Example 4, the avoidance of anesthesia, was felt to be an improvement over Example 3 in that body movement of an awake animal would keep instilled peritoneal fluids evenly distributed in order to ensure maximal effect and minimize fluid pooling.

Analysis of the animal data included provision for the elimination of data points that were obviously in error. In Example 4, any I.P. volume measurements that were in excess of 500 mL, or less than 100 mL were eliminated. In Example 4, erroneous volume determinations were recalculated by an extrapolation method from data points previous to and subsequent to the erroneous data point. The rejection of outlying data was felt to be justified as the methodology for measurement of fluid volume, an isotope dilution method, while undoubtedly the best of currently available analytical methods is fraught with a relatively high degree of variance. Since volume measurements are key to the calculation of the important efficacy parameters (ultrafiltration rate, clearance rate, and others), the rejection of expected outlying data was felt to be justified and appropriate.

The basic efficacy parameters that were monitored during the animal studies were as follows:

1. Total Intraperitoneal Fluid Volume (method: radioactive isotope dilution)
2. Dialysate Urea Concentration (Abbott Diagnostic Division (ADD), A-gent ® BUN or equivalent)
3. Plasma Urea Concentration (ADD, A-gent ® BUN or equivalent)
4. Blood Glucose (Dextrose) Concentration (ADD, A-gent ® Glucose-UV or equivalent)
5. Dialysate Glucose (Dextrose) Concentration (ADD, A-gent ® Glucose-UV or equivalent)

Microcapsule Studies

Five groups of differing microcapsules were prepared for this study. The groups and the contents of the microcapsules are shown below.

| Sample I.D. | Description |
|---|---|
| Group #1 | |
| 86:1 | Dextrose/Gelatin |
| 86:2 (Formula 2.A) | Dextrose/Gelatin (Formalin treated) |
| 86:3 | Dextrose/Gelatin (Formalin treated) |
| 86:4 | Dextrose/Sterotex |
| 86:5 | Dextrose/Gelatin (Acetone phase inversion) |
| 86:6 | Dextrose/Gelatin (Acetone phase inversion) |
| 86:7 | Dextrose/Gelatin (Emulsion method) |
| 86:8 | Dextrose/Gelatin (Span emulsion) |
| 86:9 | Hardened emulsion |

| Sample I.D. | Description |
|---|---|
| 86:10 | Dextrose/Gelatin (Hardened emulsion with Stearic Acid) |
| 86:11 | Cyanomethacrylate Microcapsules |
| 86:12 | Cyanomethacrylate on Hardened Emulsion |
| 86:13 | Hardened Emulsion variation |
| 86:26 | Phosphatide Albumin Coacervate |
| Group #2 | |
| None | "wet" Alginate microcapsules |
| None | "dry" alginate microcapsules |
| Group #3 | |
| 373-129 | Dextrose/Alginate non-solvent emulsion) |
| 373-132 | Dextrose Alginate I |
| 373-133 | Dextrose Alginate II |
| 373-134 | Dextrose Alginate III |
| 373-123 | Dextrose Microencapsulation IV |
| 373-135 | Dextrose Alginate V |
| Group #4 | |
| 16249-247A | S-100/Methocel, 70% dextrose |
| 16249-247B | S-100/Methocel, 80% dextrose |
| #5286 | HP/55/Ethocel, 80% dextrose |
| 16249-213 | S-100, 82% dextrose |
| Group #5 | |
| D652-099-1 | poly(dl-lactide), 31% dextrose |
| D652-077-1 | poly(dl-lactide), 15% dextrose |

The sustained release dextrose beads of Groups 1-5, and in particular of Group #4 can be made by the following procedures. The glucose containing controlled release system will release from about 10% to about 80% w/w dextrose within the first hour, preferably from about 10% to about 60% w/w, more preferably from about 10% to about 30% w/w.

The glucose can be purchased as glucose crystals and coated by various means to make the beads, or formulated in differing ratios as for example from 3:1 to 6:1 with a PVP (1-ethenyl-2-pyrrolidininone polymer)/$H_2O$ (water) mixture. The PVP/$H_2O$/dextrose granules are made by adding PVP slowly to water while stirring After dissolution the mixture is slowly added to the dextrose until granulation has occurred. The composition is spread and left to dry from approximately 12 to 18 hours. The granulation is then screened through about a 25 to about a 60 mesh screen. The resulting granulation is then coated with about 10% to about 40% w/w of any of the well-known water soluble or bioerodible coatings available, such as Ethocel ® (ethy cellulose) Endragit S-100 ®,HP-55 ®, Methocel ®, and the like.

Examplary formulations of the coating mixture may contain [Eudragit S-100,15.9 gms; Castrol Oil 1.8 gms; Acetone 100 ml; alcohol 100 ml; water 20 ml; and a dye 200mg] or [HP-55 35 gms; Castor oil 3 gms; Acetone 150 ml; Alcohol 150 ml; Water 20 ml; Red Dye 200 mgs]. The coating agents may be used alone or in combination with each other, such as ethylcellulose and HP-55 in equal parts by weight, and the like. The coating formulation is sprayed on to the beads by conventional means well known in the art.

After coating the particles are screened and separated. Dissolution studies are run at a pH from about 5.0 to about 5.5, 130 mEq NaCl, and a temperature of about 37 degrees centigrade.

The preparation of the Dextrose/Alginate sustained release compositions of Group #3 are prepared by various means. Sample 373-129, is a non-solvent emulsion, containing an organic phase, e.g. Miglyol 812 ®, and an aqueous phase of distilled water (100 gms); dextrose, anhydrous(10 gms); and sodium alginate LB grade (10 gms). A calcium chloride (2 gm, anhydrous) solution is sprayed into the aqueous solution. Rapid stirring is maintained as the alginate gel starts to set. Before the gel coalesces the stirring is stopped, excess liquids are decanted and a vacuum filter is used to remove additional liquids with a final drying at oven temperatures of about 50° Centigrade.

Dextrose Alginate I–III, and V, samples 373-132, 133, 134, and 135, are prepared by the following method: The formula is prepared by mixing the (anhydrous) dextrose being into the water. Stirring occurs until a clear solution is formed, and the dextrose is dissolved. Using a Ystral mill, the alginate is added (using the vortex around the 'head' to wet the alginate) to the dextrose solution. After this solution becomes homogeneous it is poured into a dropping (or separating) funnel. The alginate is then "dropped" into a calcium chloride solution to form rounded beads.

The dropping solution is allowed to produce drops for approximately 30 minutes to 2 hours. The beads produced are then removed, washed in alcohol, and tray dried at 50° C. for about 12 to about 18 hours.

The "dropping" solution, calcium chloride solution and solution contact time for Alginates I-III, and V are as follows:

Alginate I—100 gm distilled water; 10 gm dextrose, anhydrous; 10 gm alginate LB; Calcium chloride solution 50 gm $CaCl_2$; 250 gm dextrose, anhydrous; and 1000g distilled water.

Alginate II—100 gm distilled water; 25 gm dextrose, anhydrous; 10 gm alginate LB; Calcium chloride solution 50 gm $CaCl_2$; 250 gm dextrose, anhydrous; and 1000 g distilled water; 30 minute contact time for bead formation.

Alginate III—100 gm distilled water; 25 gm dextrose, anhydrous; 10 gm alginate LB; Calcium chloride solution 50 gm $CaCl_2$; 250 gm dextrose, anhydrous; and 1000 g distilled water; 2 hour contact time for bead formation.

Alginate V—100 gm distilled water; 100 gm dextrose, anhydrous; 10 gm alginate LB; Calcium chloride solution: 50 gm $CaCl_2$; 100 gm dextrose, anhydrous; and 1000 gm distilled water; 2 hour contact time for bead formation.

Microencapsulation sample 373-123 is produced by the Fanger technique. 500 ml of cyclohexane is put into a flat bottomed dissolution flask with a five neck glass seal. Three of the seals are blocked off with ground glass stoppers and the fourth has a condenser attached for reflux of the cyclohexane. A paddle is placed into the center neck and is of suitable size to create a good vortex at a stirring speed of 400 rpm.

The flask is placed on a hotplate and when the cyclohexane is hot, 5 gm of ethylcellulose is added. When dissolved, 10 gm anhydrous dextrose is added and refluxed for 1 hour. After cooling the cyclohexane is decanted. The microcapsules are then dried by a stream of compressed air under controlled conditions to prevent aggregation.

The samples of Group #1 were supplied by the University of Oklahoma, College of Pharmacy, Oklahoma City, Okla. The samples of Group #2 were supplied by Karyon Technology, Norwood, Mass., and the sustained release microcapsules of Group #5 were supplied by Southern Research Institute, Birmingham, Ala.

Each of the microcapsule preparations was evaluated as to its in vitro dissolution profile From these data, selected microcapsule batches were subjected to in situ animal studies A calculated aliquot of microcapsules, sufficient to provide the total dextrose release observed in animal pump studies was dispersed in the primary instillation fluid and instilled intraperitoneally at time zero. The same efficacy parameters as in the pump experiments were monitored. Additionally, selected animals were sacrificed for gross pathology examination after the conclusion of microcapsule controlled peritoneal dialysis.

Results

A. Pump Studies

Example 3 "Pump" Studies

Figure 5:
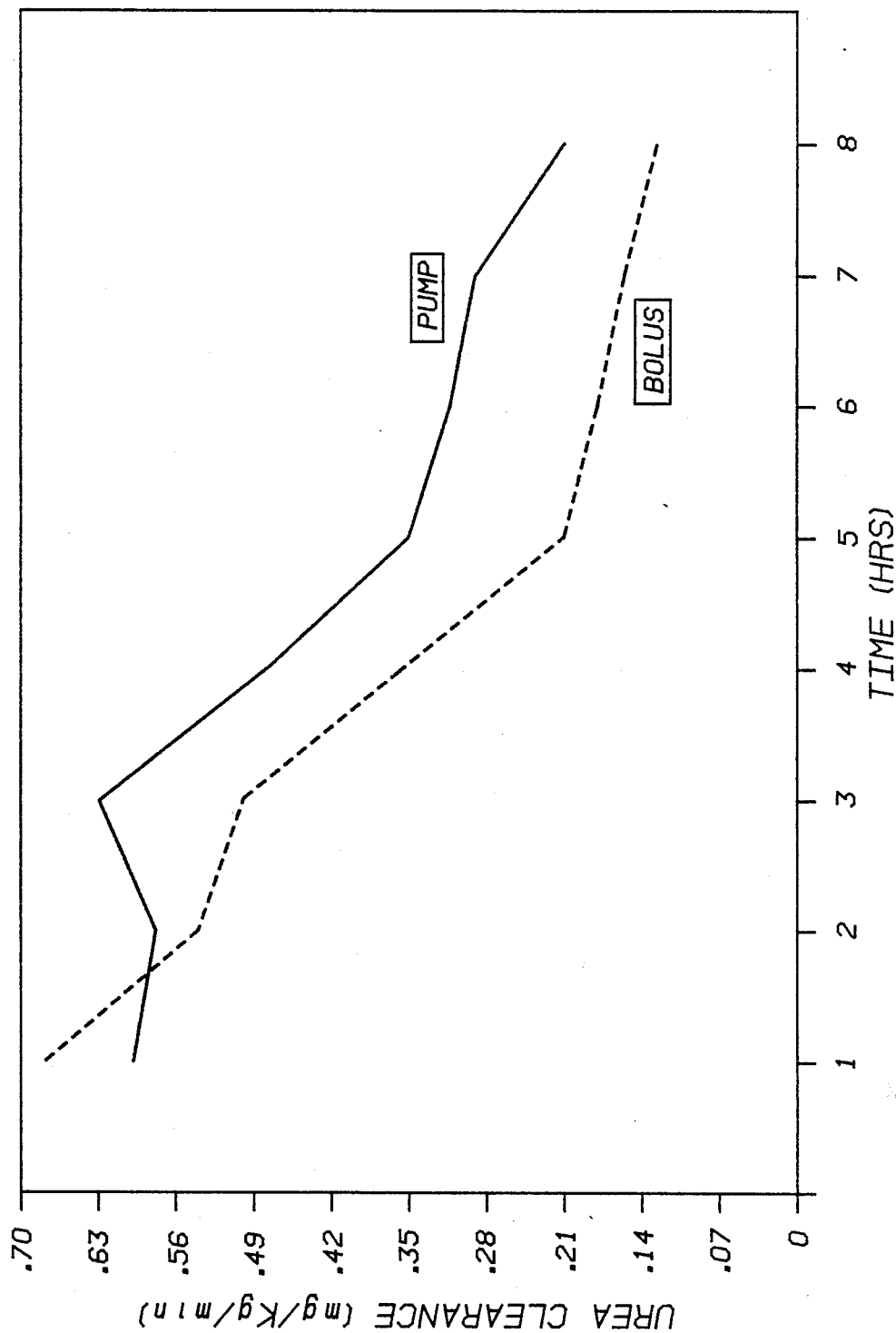
FIGS. 5 through 7 illustrate the differences between the "pump" animals treated with the method of this invention, and animals treated with the conventional CAPD "bolus" method of the prior art for urea clearance, ultrafiltration rate and dialysate volume.
Figure 6:
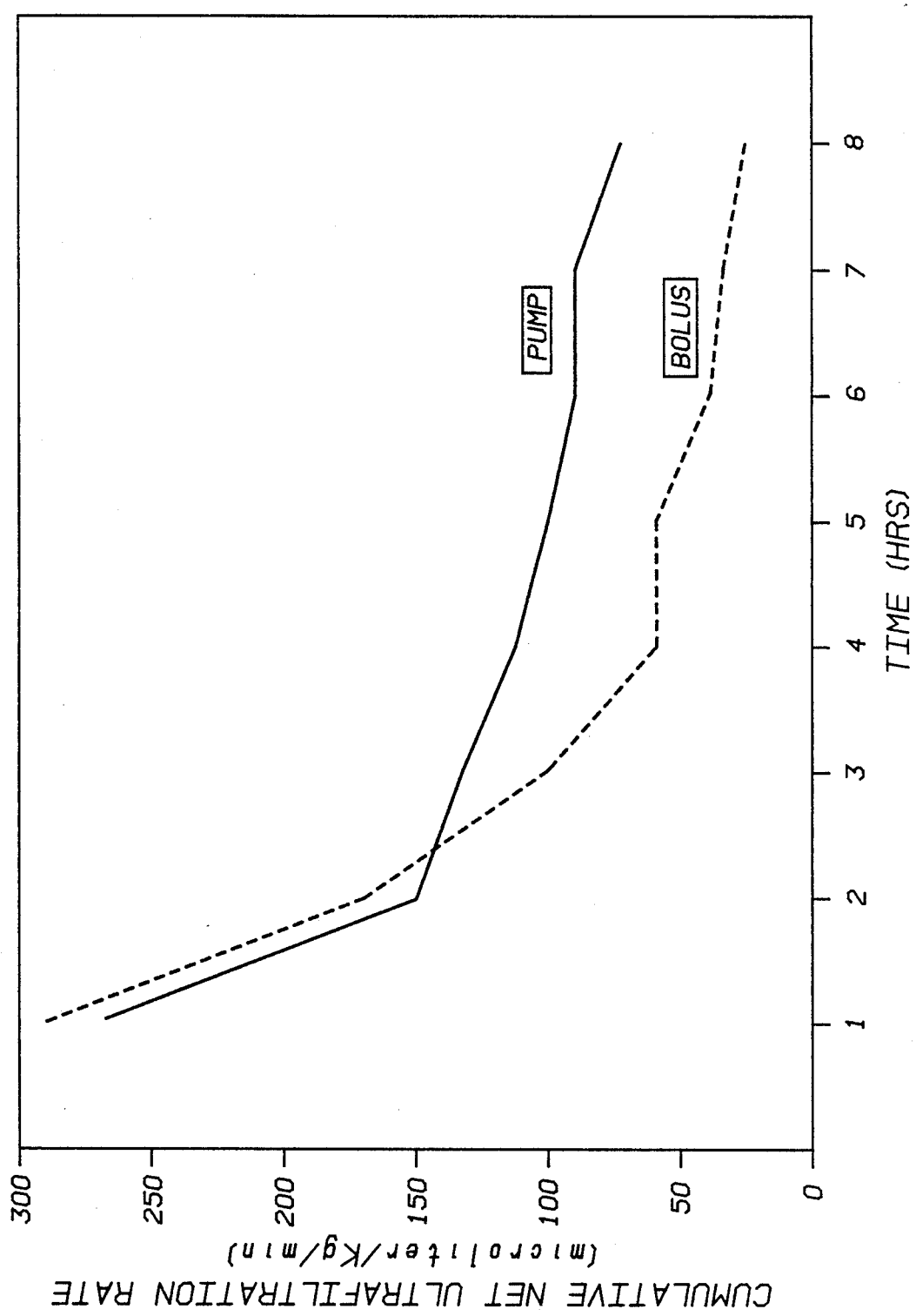
Figure 7:
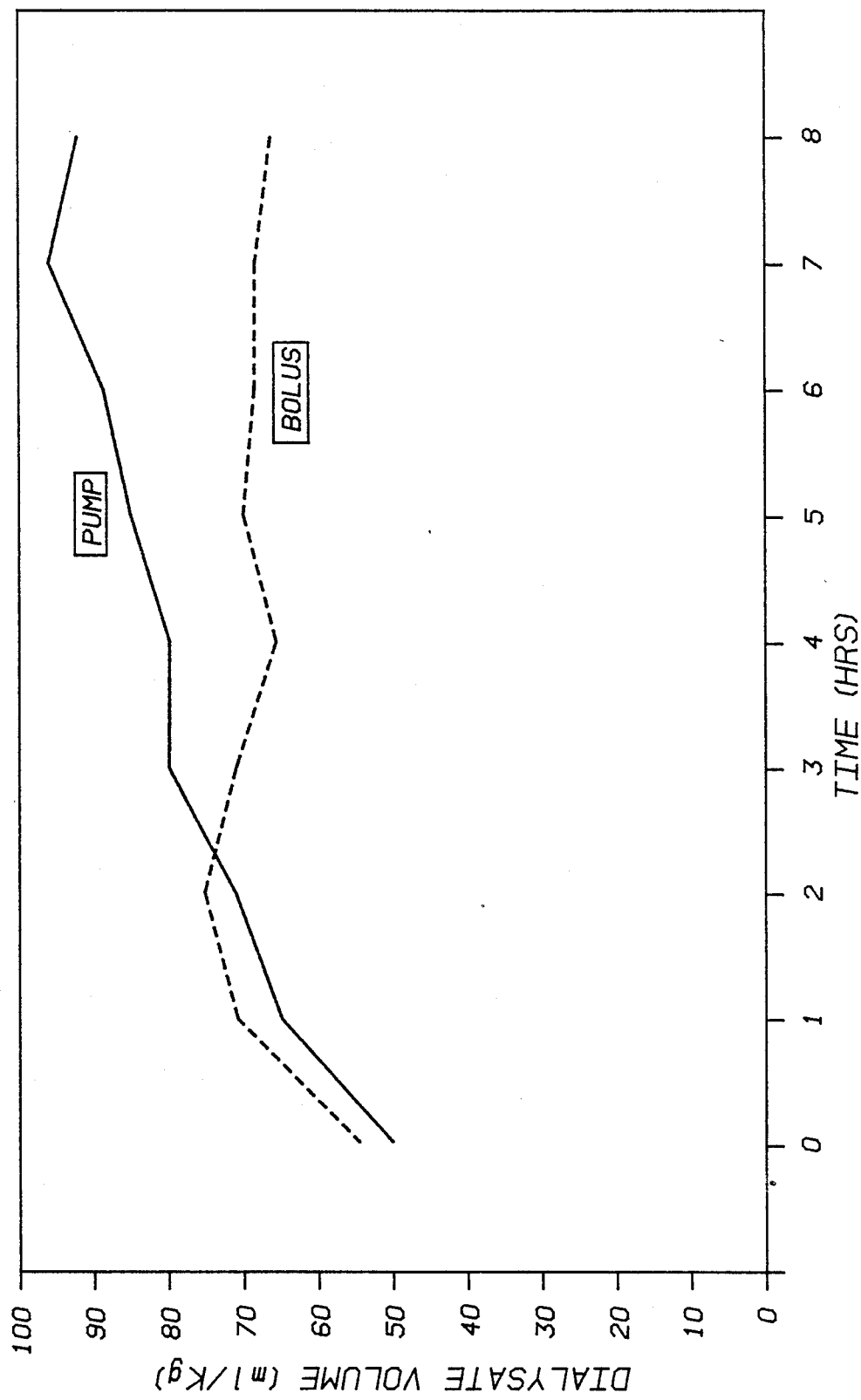
Figure 8:
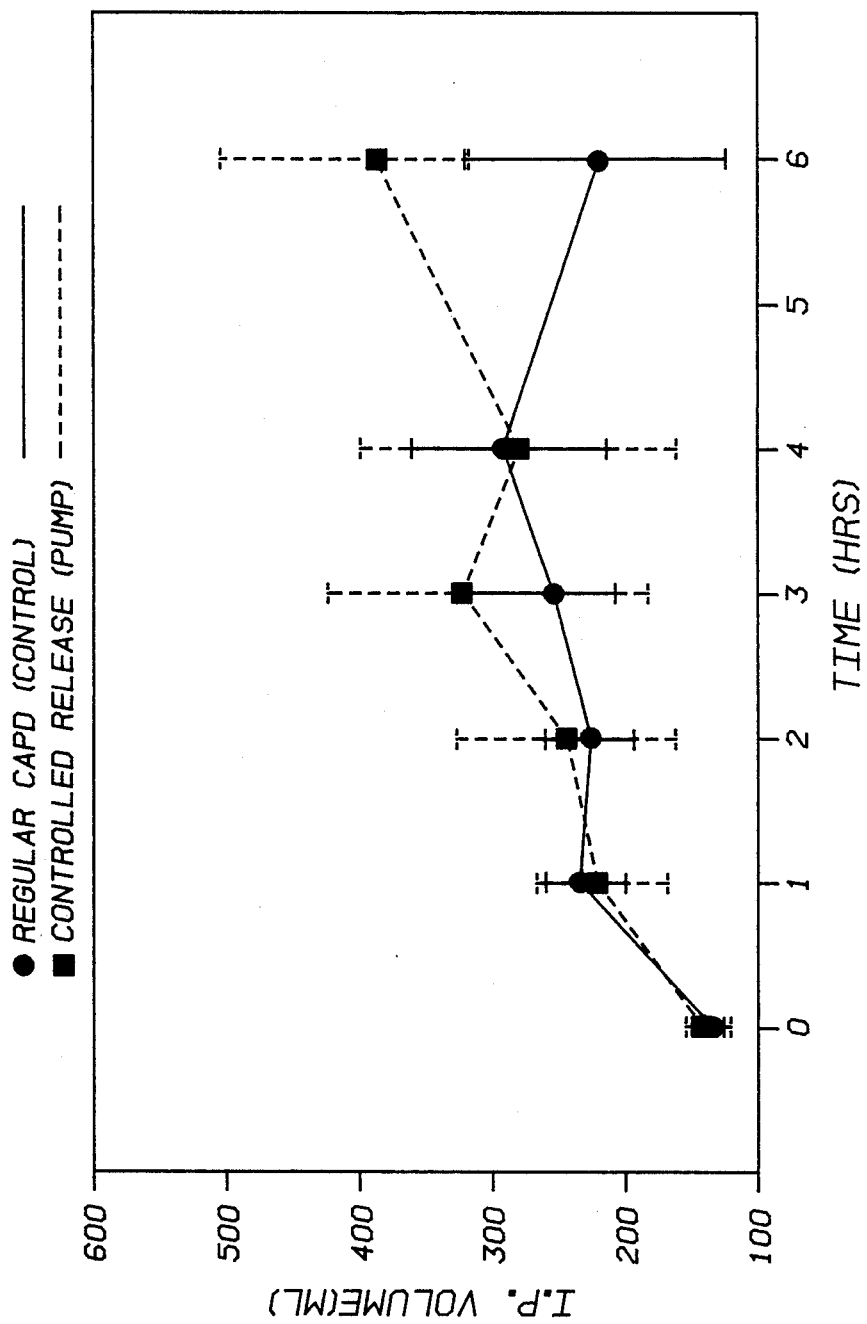
FIGS. 8 through 11 illustrate a summary of data collected from control animals (conventional CAPD) and the "pump" animals for I.P. volumes and ultrafiltration rates.
Figure 9:
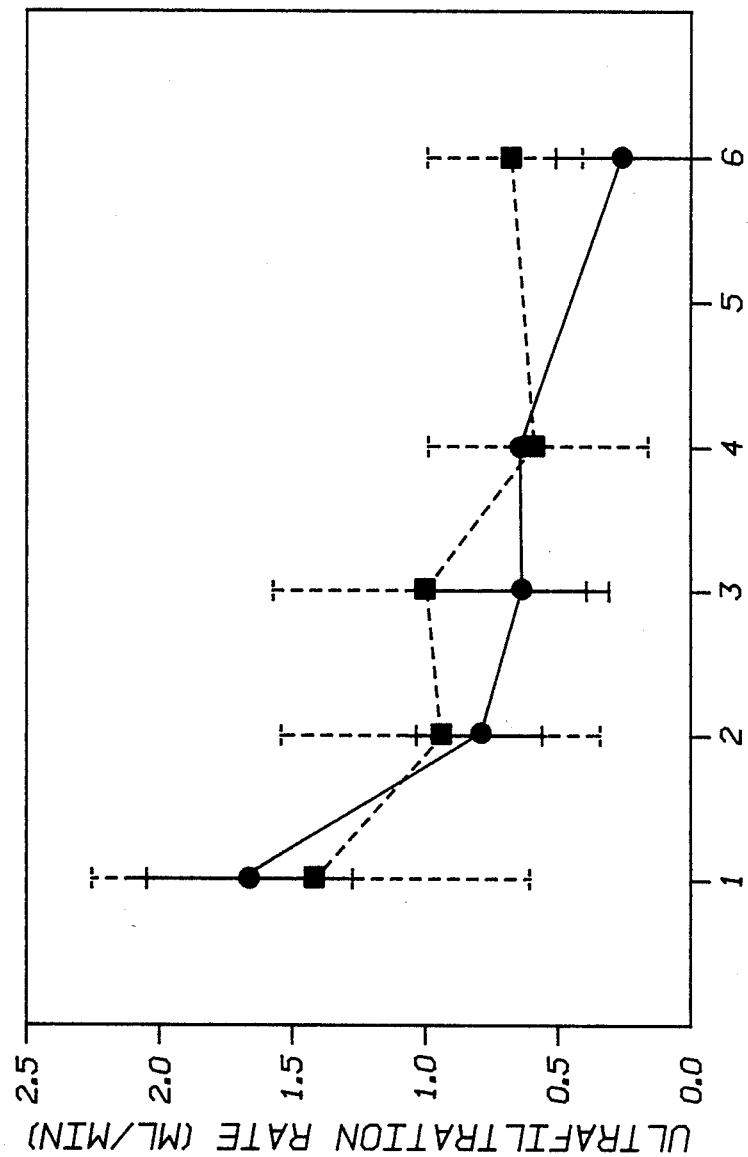
Figure 10:
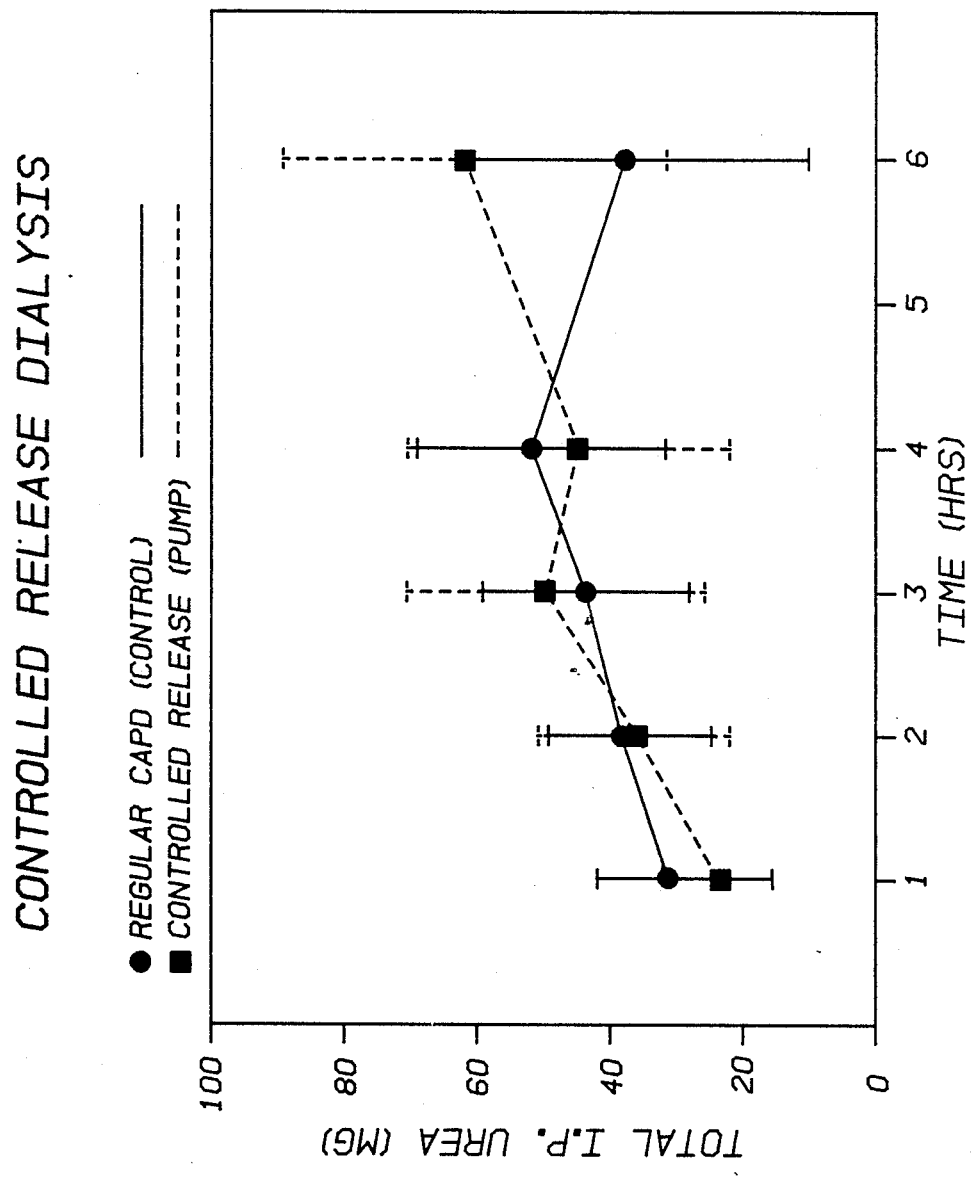
Figure 11:
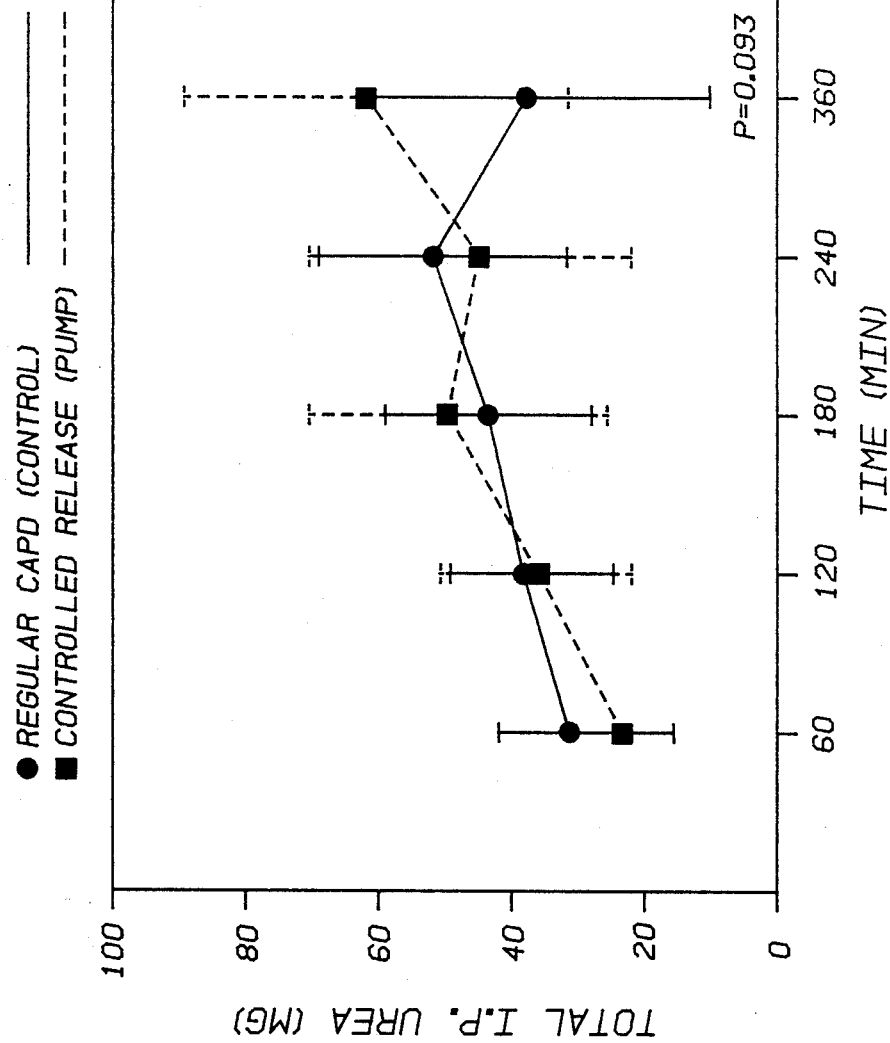

FIGS. 5, 6 and 7 illustrate the differences between the "pump" animals and single conventional CAPD ("Bolus") animals with respect to urea clearance, ultrafiltration rate, and dialysate volume. Significant statistical difference by paired t test (p less than 0.05) between the animals when undergoing pump and bolus studies exists in all three parameters by the eighth experimental hour, with the pump animals exhibiting clear increases in urea clearance, ultrafiltration, and dialysis volume.

Example 4 "Pump" Studies

FIGS. 8, 9, 10 and 11 illustrate a summary of the data collected from ten control animals (regular CAPD 2.5 percent) and nine "pump" animals (70 percent dextrose, 2 ml/hr). A significant statistical difference between the "pump" animals and the regular CAPD control animals existed by the sixth study hour with respect to I.P. (dialysate) volume and ultrafiltration rate (urea clearance and total intraperitoneal urea possessed "p" values of between 0.1 and 0.05).

FIG. 12 compares, in tabular form, the efficacy parameters of regular CAPD to those of controlled release CAPD observed in this study. It is interesting to note that both the ultrafiltration rate and the urea clearance rate are significantly increased with the controlled release system as compared to the control animals evaluated both as an average over 6 hours and at the 6-hour datum point. These data indicate that the controlled release of the osmotic agent increases the efficiency of the peritoneal dialysis process over regular CAPD (the control animals).

FIG. 13 illustrates the differences in Blood Glucose Concentration versus Time for both regular CAPD and controlled release CAPD. Blood Glucose levels were significantly elevated in the pump group versus control for all experimental time intervals.

B. In-Vivo Microcapsule Studies

Figure 14:
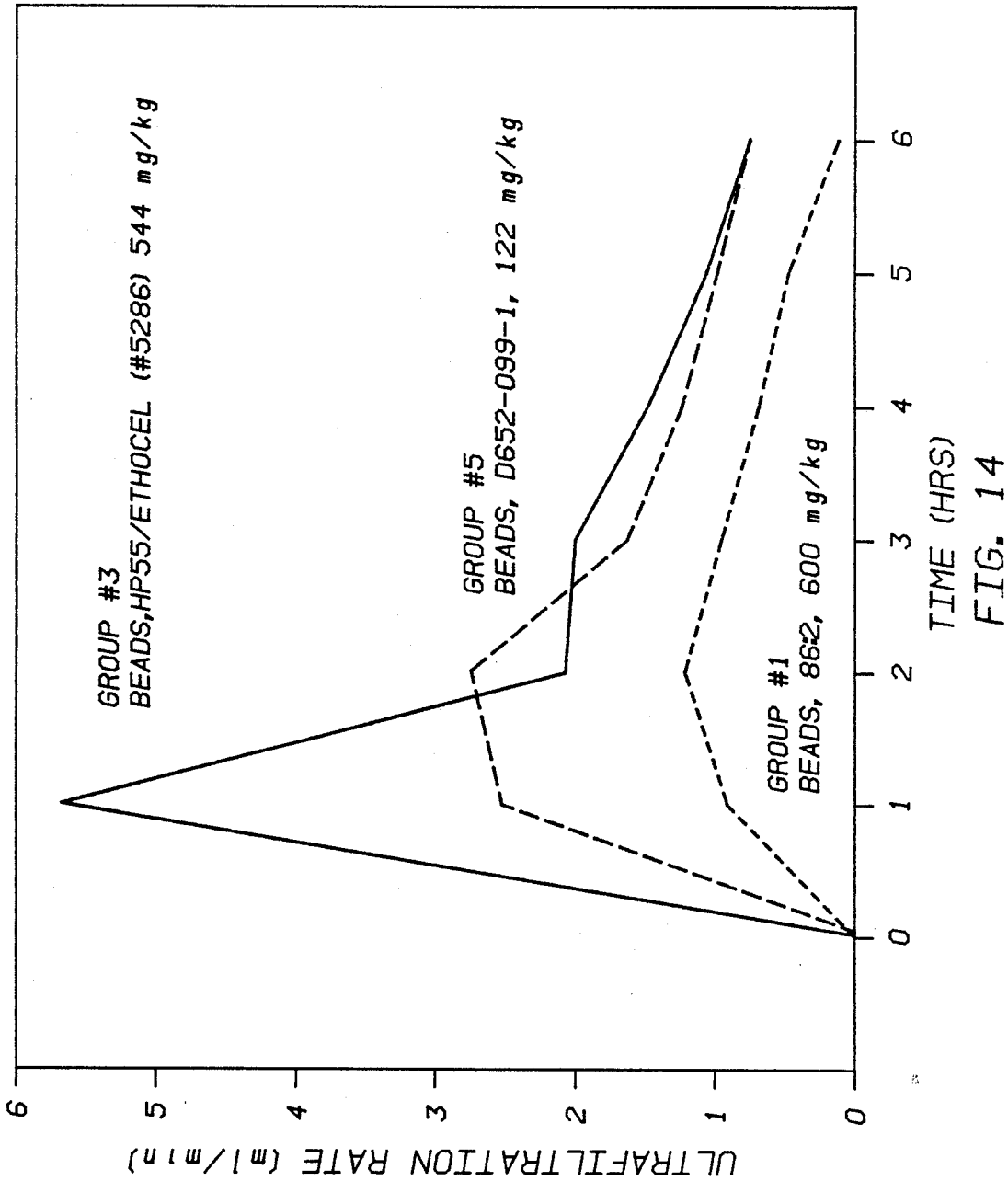
FIGS. 14 through 16 illustrate microcapsule systems and FIG. 17 provides an in-vitro dissolution profile of the three microcapsules of FIGS. 14 through 17.
Figure 15:
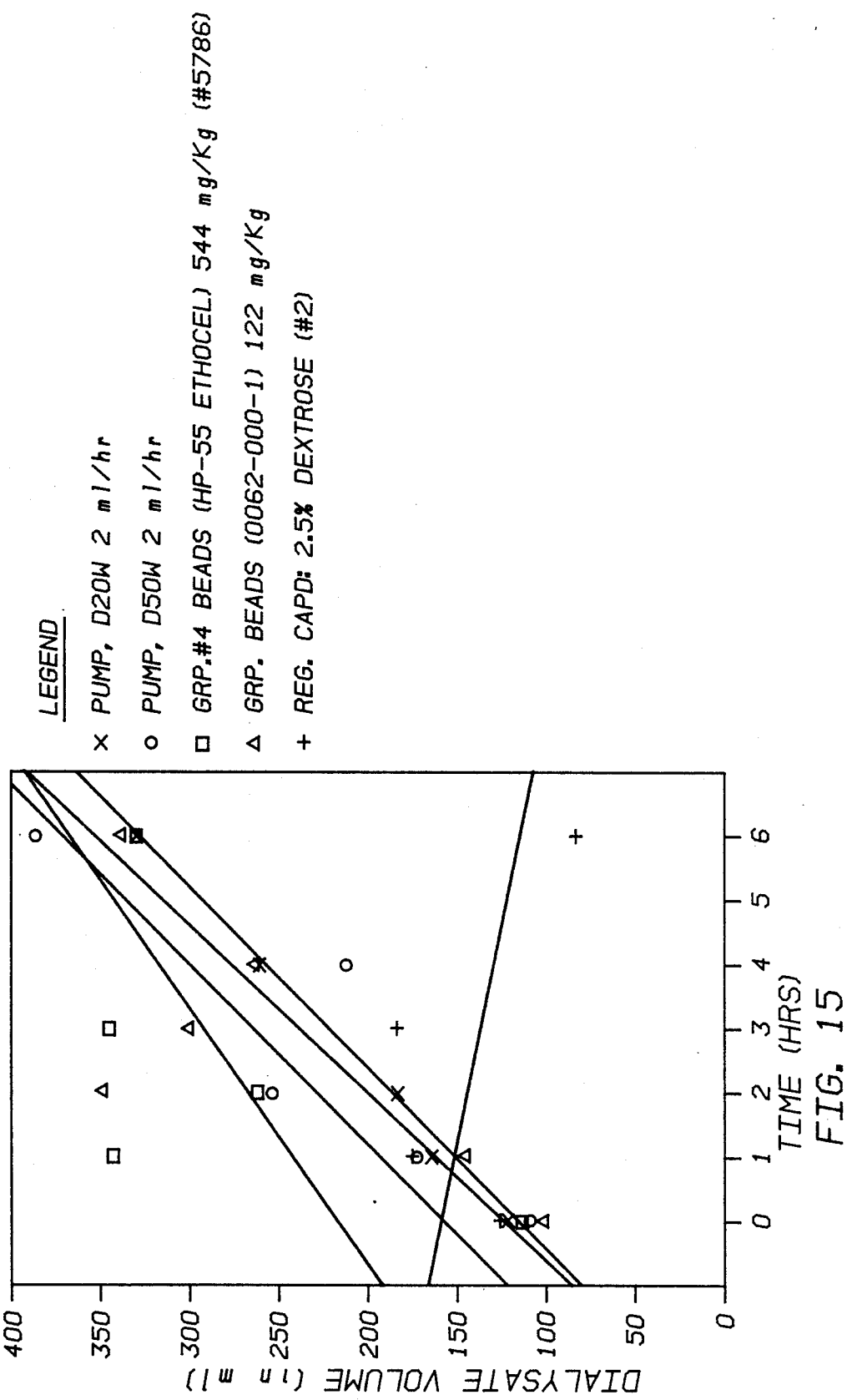
Figure 16:
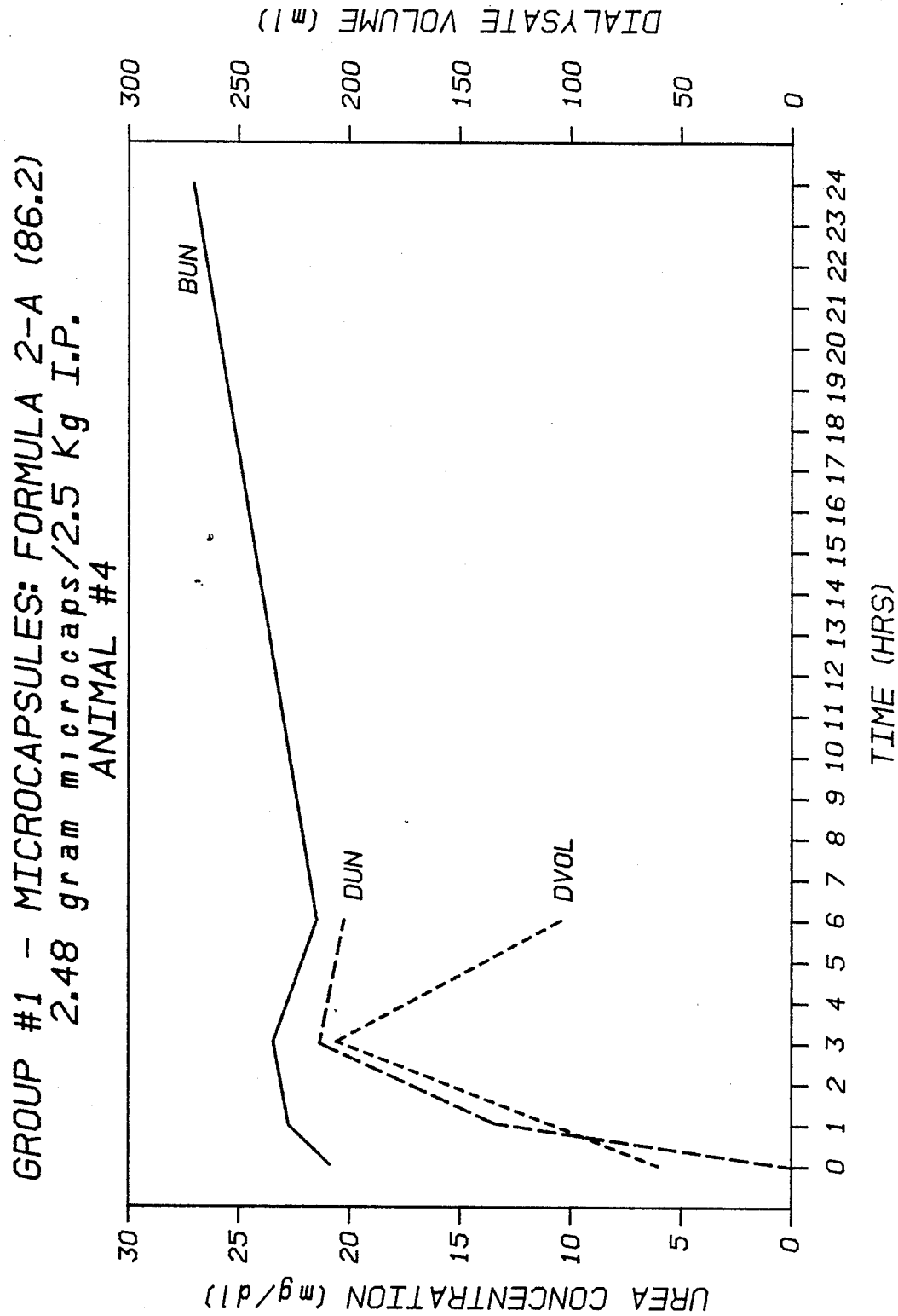
Figure 17:
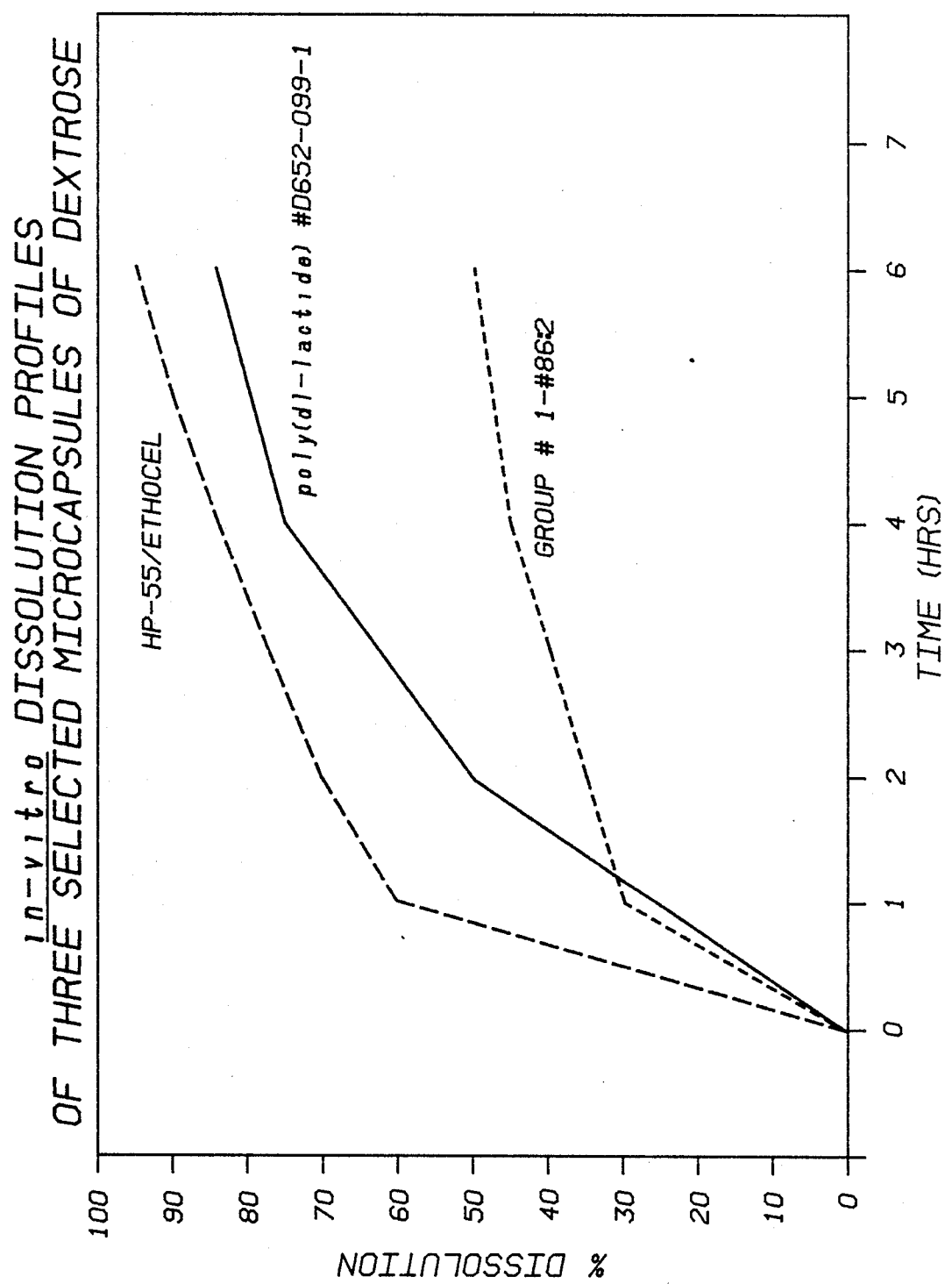
FIG. 17 shows In Vitro Dissolution Profiles of Three Selected Microcapsules of Dextrose in percent Dissolution versus Time [in hours].

FIGS. 14, 15 and 16 illustrate the efficacy of three dextrose microcapsule systems in peritoneal dialysis In terms of ultrafiltration rate, dialysate volume and dialysate urea concentration, the microcapsule systems evaluated compare favorably to the "pump" studies and in all monitored efficacy parameters exceeded those exhibited by regular CAPD fluids by the second study hour. The in vivo dissolution profiles of these three selected microcapsule formulations is illustrated in FIG. 17.

In each of the in vivo studies conducted with the microcapsule systems, the animals were sacrificed at the conclusion of the studies in order to do a gross pathological examination of the peritoneal cavity and membrane. There was no evidence of pathological changes noted within the peritoneal cavity. However, substantial aggregation of the microcapsules was noted. The significance of this intra-peritoneal aggregation, if any, on the efficacy of the preparations was not assessed.

Based on the data generated in these studies, the following conclusions can be made:

First, the controlled release of soluble osmotic agent into the peritoneal cavity resulted in a demonstable increase in efficacy of the dialysis process over that seen with regular peritoneal dialysis fluids. Demonstrable and significant increases in efficacy parameters monitored (ultrafiltration rate, urea clearance rate, and dialysate volume) were observed in in vivo studies comparing controlled released peritoneal dialysis to regular peritoneal dialysis.

Second, the controlled release of osmotic agent can be accomplished by either a precision pump or a pharmaceutical (microcapsule) system.

Third, several pharmaceutical (microcapsule) formulations have been shown to produce controlled release in vitro.

Although the scope of this study was limited to the "proof-of-principle" of a controlled release dextrose dialysis fluid, the applicability of both the pump and microcapsule configuration to the controlled release of intraperitoneally administered drug substances is evident.

The foregoing specification, including the specific embodiments and examples is intended to be illustrative of the present invention and is not to be taken as limiting. Numerous other variations and modifications can be effected without departing from the true spirit and scope of the present invention.

That which is claimed is:

1. A method for peritoneal dialysis of a patient in need of such treatment, comprising the steps of
    (a) establishing fluid communication through the peritoneal membrane into the peritoneal cavity;
    (b) instilling an initial volume of an aqueous peritoneal dialysis composition containing an osmotic agent into the peritoneal cavity through said fluid communication, said dialysis composition containing an amount of dissolved osmotic agent
        (i) that is insufficient to adequately dialyze said patient during a predetermined time period of dialysis treatment, but
        (ii) that is present at an osmolarity that is greater than the osmolarity of the body fluids in contact with said membrane,
    such that an osmolarity gradient is created across said membrane between said composition and said body fluids by means of which gradient a flux of water and solute enters said composition from said body fluids;
    (c) continually releasing additional dissolved osmotic agent into the instilled dialysis composition to form a modified dialysis composition, said additional osmotic agent being released in an amount sufficient to maintain a substantially constant osmolarity gradient between said modified dialysis composition and said body fluids such that said water and solute flux continues to enter into said modified dialysis composition during said predetermined dialysis time period; and
    (d) substantially removing the modified dialysis composition from the peritoneal cavity at the end of said time period.

2. The method according to claim 1 further including repeating steps (b) through (d) continuously thereafter, so long as the patient is in need of such treatment.

3. The method according to claim 1 wherein said osmotic agent is released into the instilled composition and modified composition at a rate sufficient to maintain the osmolarity of the modified dialysis composition at from about 300 mOsm/L to about 500 mOsm/L.

4. The method according to claim 1 wherein the initial volume of aqueous peritoneal dialysis composition instilled into the peritoneal cavity has an osmolarity of from about 300 mOsm/L to about 500 mOsm/L.

5. The method according to claim 1 wherein the initial volume of dialysis composition instilled is from about 0.1 to about 1.0 liters.

6. The method according to claim 1 wherein said further dissolved osmotic agent is released into said instilled composition and modified composition from a reservoir of osmotic agent composition external to the peritoneal cavity by pumping means external to the peritoneal cavity.

7. The method according to claim 6 wherein the present osmotic agent composition has a concentration of from about 50 percent w/v to about 90 percent w/v of osmotic agent.

8. The method according to claim 6 wherein the pumping means is a wearable, electrically powered pump.

9. The method according to claim 8 wherein said osmotic agent is released into said instilled composition and modified composition at a rate sufficient to maintain the modified dialysis composition osmolarity at from about 300 mOsm/L to about 500 mOsm/L.

10. The method according to claim 1 wherein said osmotic agent is sequestered, in a controlled release form, and the sequestering agent is a member selected from the group consisting of polylactic acid polymers, cellulose, cellulose derivatives, gelatin, and polyglycolic acid polymers.

11. The method according to claim 1 wherein the osmotic agent is selected from the group consisting of sugars, sugar alcohols, sugar polymers, amino acids, alpha-keto analogs of amino acids, alpha-keto salts of amino acids, plasma proteins, phosphatides and combinations thereof.

12. A method for peritoneal dialysis of a patient in need of such treatment, comprising the steps of:
(a) establishing fluid communication through the peritoneal membrane into the peritoneal cavity;
(b) instilling an initial volume of an aqueous peritoneal dialysis composition containing an osmotic agent into the peritoneal cavity through said fluid communication, said dialysis composition containing an amount of dissolved osmotic agent
  (i) that is insufficient to adequately dialyze said patient during a predetermined time period of dialysis treatment, but
  (ii) that is present at an osmolarity that is greater than the osmolarity of the body fluids in contact with said membrane, such that an osmolarity gradient is created across said membrane between said composition and said body fluids by means of which gradient a flux of water and solute enters said composition from said body fluids;
(c) continually releasing additional dissolved osmotic agent into the instilled dialysis composition to form a modified dialysis composition, said additional osmotic agent being in a controlled release form, and released in an amount sufficient to maintain a substantially constant osmolarity gradient between said modified dialysis composition and said body fluids such that said water and solute flux continue to enter into said modified dialysis composition during said predetermined dialysis time period; and
(d) substantially removing the modified dialysis composition from the peritoneal cavity at the end of said time period.

13. The method according to claim 12 including further repeating steps (b) through (d) continuously thereafter, so long as the patient is in need of such treatment.

14. The method according to claim 12 wherein the additional osmotic agent, in a controlled release form, is present in the initially instilled volume the total amount needed for said predetermined dialysis time period 15. The method according to claim 12 wherein the further osmotic agent, in a controlled release form, is released into said instilled composition and modified composition in the total amount needed for the predetermined dialysis time by a second instillation, into the peritoneal cavity.

16. The method according to claim 12 wherein the said osmotic agent in a controlled release form is sequestered, and the sequestering agent is a member selected from the group consisting of polyactic acid polymers, cellulose, cellulose derivatives, gelatin, and polyglycolic acid polymers.

17. The method according to claim 12 wherein said osmotic agent is released into said instilled composition and modified composition at a rate sufficient to maintain the osmolarity of the modified dialysis composition at from about 300 mOsm/L to about 500 mOsm/L.

18. The method according to claim 12 wherein said controlled release form is microencapsulated.

19. A method for peritoneal dialysis of a patient in need of such treatment, comprising the steps of:
(a) establishing a fluid communication through the peritoneal membrane into the peritoneal cavity;
(b) instilling an initial volume of an aqueous peritoneal dialysis composition containing an osmotic agent into the peritoneal cavity through said fluid communication, said dialysis composition containing an amount of dissolved osmotic agent
  (i) that is insufficent to adequately dialyze said patient during a predetermined time period of dialysis treatment, but
  (ii) that is present at an osmolarity that is greater than the osmolarity of the body fluids in contact with said membrane, such that an osmolarity gradient is created across said membrane between said composition and said body fluids by means of which gradient a flux of water and solute enters said composition from said body fluids;
(c) continually releasing further dissolved osmotic agent into the instilled dialysis composition from a reservoir of osmotic agent composition, external to the peritoneal cavity by pumping means external to the peritoneal cavity, to form a modified dialysis composition, said further osmotic agent being released in an amount sufficient to maintain a substantially constant osmolarity gradient between said modified dialysis composition and said body fluids such that said water and solute flux continue to enter into said modified dialysis composition during said predetermined dialysis time period; and
(d) substantially removing the modified dialysis composition from the peritoneal cavity at the end of said time period.

20. The method according to claim 19 further including repeating steps (b) through (d) continuously thereafter, so long as the patient is in need of such treatment.

21. The method according to claim 19 wherein said osmotic agent is released into the instilled composition at a rate sufficient to maintain the osmolarity of the modified dialysis composition at from about 300 mOsm/L to about 500 mOsm/L.

22. The method according to claim 19 wherein the external reservoir of osmotic agent composition has a concentration of from about 50 percent w/v to about 90 percent w/v.

23. The method according to claim 19 wherein the pumping means is a wearable, electrically powered pump.

24. A method for peritoneal dialysis of a patient in need of such treatment, comprising the steps of:
(a) establishing a fluid communication through the peritoneal membrane into the peritoneal cavity;
(b) instilling an initial volume of an aqueous peritoneal dialysis composition containing an osmotic agent into the peritoneal cavity through said fluid communication, said dialysis composition containing an amount of dissolved osmotic agent
  (i) that is insufficent to adequately dialyze said patient during a predetermined time period of dialysis treatment, but
  (ii) that is present at an osmolarity that is greater than the osmolarity of the body fluids in contact with said membrane, such that an osmolarity gradient is created across said membrane between said composition and said body fluids by means of which gradient a flux of water and solute enters said composition from said body fluids;
(c) continually instilling a second aqueous dialysis composition containing a further dissolved osmotic agent into the first-named instilled dialysis composition from a reservoir of osmotic agent composition external to the peritoneal cavity by pumping means external to the peritoneal cavity, to form a modified dialysis composition, said further osmotic agent being released in an amount sufficient to maintain a substantially constant osmolarity gradient between said modified dialysis composition and said body fluids such that said water and solute flux continue to enter into said modified dialysis composition during said predetermined dialysis time period; and
(d) removing the modified dialysis composition from the peritoneal cavity at a substantially similar rate to the instillation of said further osmotic agent; and
(e) substantially removing any remaining modified dialysis composition from the peritoneal cavity at the end of said time period.

* * * * *